United States Patent
Liu et al.

(10) Patent No.: US 11,084,830 B2
(45) Date of Patent: Aug. 10, 2021

(54) FIVE-MEMBERED NON AROMATIC RING-PYRIMIDINE HIV-1 REVERSE TRANSCRIPTASE INHIBITOR, PREPARATION METHOD THEREFOR, AND USES THEREOF

(71) Applicant: SHAN DONG UNIVERSITY, Jinan (CN)

(72) Inventors: Xinyong Liu, Jinan (CN); Dongwei Kang, Jinan (CN); Peng Zhan, Jinan (CN); Gaoshan Wu, Jinan (CN); Zhao Wang, Jinan (CN)

(73) Assignee: SHAN DONG UNIVERSITY, Jinan (CN)

( * ) Notice: Subject to any disclaimer, the term of this patent is extended or adjusted under 35 U.S.C. 154(b) by 0 days.

(21) Appl. No.: 16/765,095

(22) PCT Filed: Oct. 12, 2018

(86) PCT No.: PCT/CN2018/110128
§ 371 (c)(1),
(2) Date: May 18, 2020

(87) PCT Pub. No.: WO2019/196370
PCT Pub. Date: Oct. 17, 2019

(65) Prior Publication Data
US 2020/0361954 A1    Nov. 19, 2020

(30) Foreign Application Priority Data
Apr. 12, 2018   (CN) .......................... 201810336405.0

(51) Int. Cl.
| | |
|---|---|
| *A61K 31/519* | (2006.01) |
| *C07D 495/04* | (2006.01) |
| *A61P 31/18* | (2006.01) |
| *C07D 401/12* | (2006.01) |
| *C07D 491/048* | (2006.01) |

(52) U.S. Cl.
CPC ............ *C07D 495/04* (2013.01); *A61P 31/18* (2018.01); *C07D 401/12* (2013.01); *C07D 491/048* (2013.01)

(58) Field of Classification Search
None
See application file for complete search history.

(56) References Cited

FOREIGN PATENT DOCUMENTS

CN            104926829 A    *   6/2015    ........... A61K 31/519

* cited by examiner

*Primary Examiner* — Samantha L Shterengarts
(74) *Attorney, Agent, or Firm* — CBM Patent Consulting, LLC

(57) ABSTRACT

The present invention belongs to the field of pharmaceutical technology, specifically disclosing five-membered non-aromatic pyrimidines compounds with the general formulas I. Also including theirs polycrystalline and eutectic, prodrugs and derivatives with same biologically functional, methods for their preparation, and compositions containing one or more of these compounds in the drugs application of treatment and prevention of human immunodeficiency virus.

5 Claims, No Drawings

FIVE-MEMBERED NON AROMATIC RING-PYRIMIDINE HIV-1 REVERSE TRANSCRIPTASE INHIBITOR, PREPARATION METHOD THEREFOR, AND USES THEREOF

FIELD OF THE INVENTION

The present invention relates to five-membered non-aromatic derivatives, pharmaceutically acceptable additional salts or prodrugs having HIV replication inhibiting properties. Also described herein are the preparation of these derivatives and pharmaceutical compositions comprising them.

BACKGROUND OF THE INVENTION

Acquired immune deficiency syndrome (AIDS) is infected by human immunodeficiency virus type 1 (HIV-1), which could cause defects in the body's defense functions (especially cell-mediated immune functions). It is prone to opportunistic infections and tumors, belonging to one of the 10 major diseases that seriously endanger the people's health. At present, China's HIV/AIDS epidemic has entered a period of rapid growth, and the number of infected people has exceeded 700,000. Although the universal implementation of high-efficiency antiretroviral therapy (HAART) has greatly reduced the AIDS morbidity and mortality, the toxic and side effects and cross-resistance caused by long-term medication have greatly restricted its clinical application. Therefore, the development of new anti-AIDS drugs is still a major scientific research task.

In the life cycle of HIV-1, reverse transcriptase (RT) is responsible for reverse transcription of single-stranded RNA carrying viral genetic information into double-stranded DNA, which is a key target for anti-AIDS drug design. RT inhibitors mainly divided into nucleos(t)ide reverse transcriptase inhibitors (N(t)RTIs) and non-nucleoside RT inhibitors (NNRTIs). Among them, NNRTIs is an important part of HAART for its advantages of high efficiency and low toxicity compared to N(t)RTIs. However, due to the high variability of HIV-1 virus, the rapid emergence of drug-resistant strains in the clinic significantly reduced their clinical efficacy. The problem of drug resistance has become an insurmountable gap for anti-AIDS drugs. Therefore, the development of a new generation of highly effective anti-drug NNRTIs is one of the important areas of anti-AIDS drug research.

Diarylpyrimidine (DAPY) is a typical type of HIV-1 NNRTIs and has promising anti-resistance profiles, both the second-generation HIV-1 NNRTIs Etravirine (ETR) and Rilpivirne (RPV) are belongs to DAPY derivatives. The use of diarylpyrimidine compounds as templates and extensive structural modifications are of great significance for the discovery of new anti-HIV drugs with high-efficiency, broad-spectrum resistance, good bioavailability, and independent intellectual property rights.

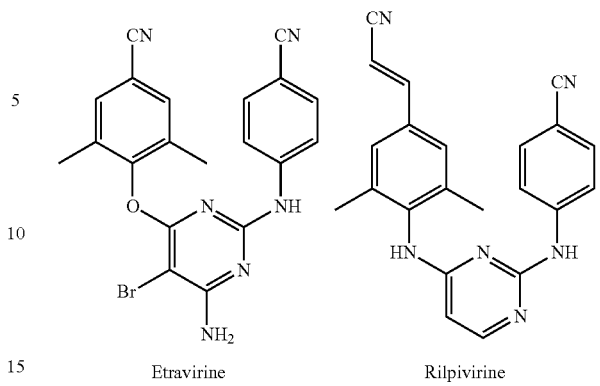

Etravirine

Rilpivirine

SUMMARY OF THE INVENTION

In view of the deficiencies of the prior art, the present invention provides a series of thiazolopyrimidine five-membered non-aromatic pyrimidines derivatives and their preparation method, as well as their applications as HIV-1 inhibitors.

1. Five-Membered Non-Aromatic Pyrimidines Derivatives

The invention provides a series of thiazolopyrimidine five-membered non-aromatic pyrimidines compounds of formula I, and pharmaceutically acceptable additional salts or prodrugs.

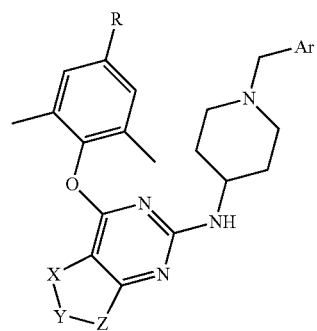

I

Wherein
R is $CH_3$, CN or CH=CHCN;
X is C, N, O, or S;
Y is C, N, O, or S;
Z is C, N, O, or S;
And at least two of X, Y and Z are C atoms at the same time;
Ar is phenyl or pyridyl; or $SO_2NH_2$, $SO_2CH_3$, $CONH_2$, halogen, $NO_2$, CN, $NH_2$, $CF_3$, $NHCH_3$, OH, COOH, $CH_2OH$, $CO_2Me$, $OCH_3$, and $NHCOCH_3$ substituted phenyl; substituents are ortho, meta and para single or multiple substitutions.

more preferably, five-membered non-aromatic pyrimidines derivatives are compounds as follows:

编号

| 结构式编号 | |
|---|---|
| A1 | 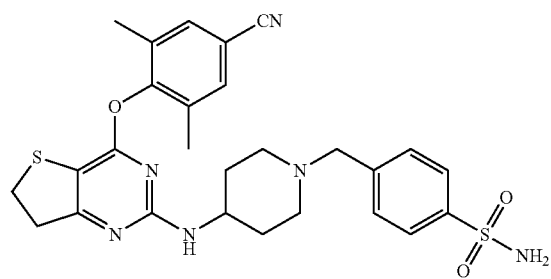 [SMILES: Cc1cc(C#N)cc(C)c1Oc1nc(NC2CCN(Cc3ccc(S(N)(=O)=O)cc3)CC2)nc2c1SCC2] |
| A2 | 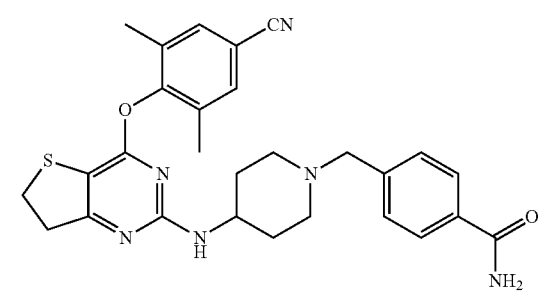 |
| A3 | 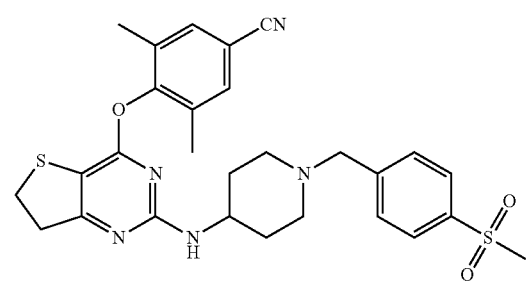 |
| A4 | 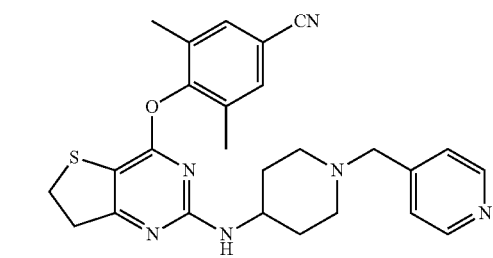 [SMILES: Cc1cc(C#N)cc(C)c1Oc1nc(NC2CCN(Cc3ccncc3)CC2)nc2c1SCC2] |
| A5 | 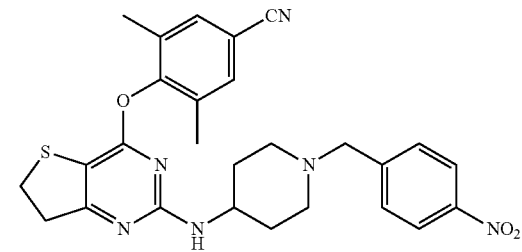 [SMILES: Cc1cc(C#N)cc(C)c1Oc1nc(NC2CCN(Cc3ccc([N+](=O)[O-])cc3)CC2)nc2c1SCC2] |
| A6 | 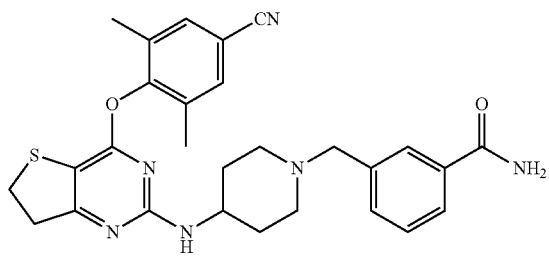 [SMILES: Cc1cc(C#N)cc(C)c1Oc1nc(NC2CCN(Cc3cccc(C(N)=O)c3)CC2)nc2c1SCC2] |
| B1 | 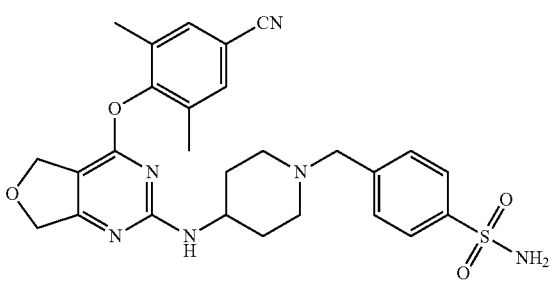 |
| B2 | 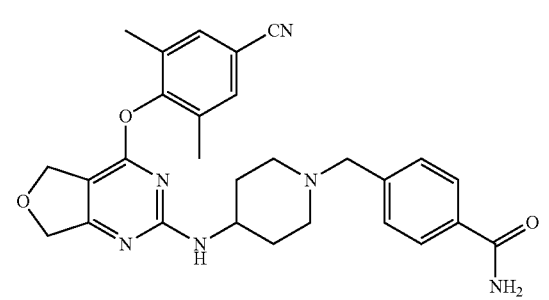 |
| B3 | 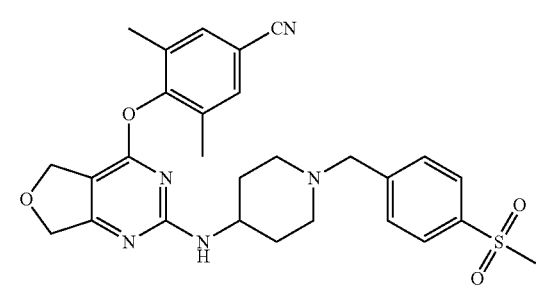 |
| B4 | 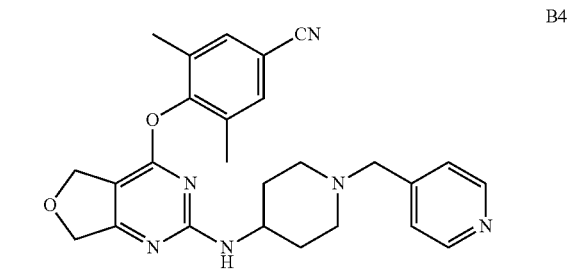 |

B5
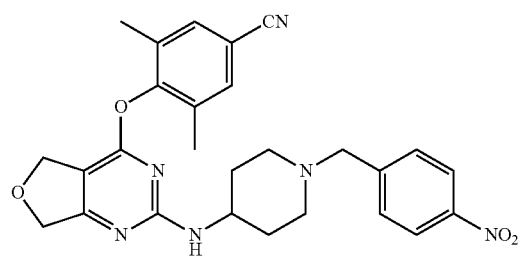

B6
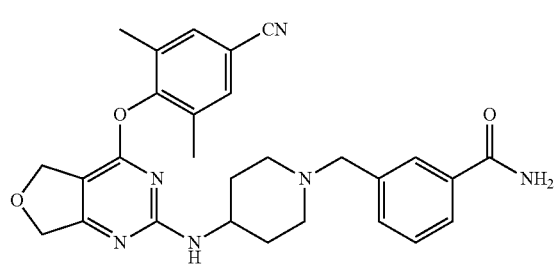

C1
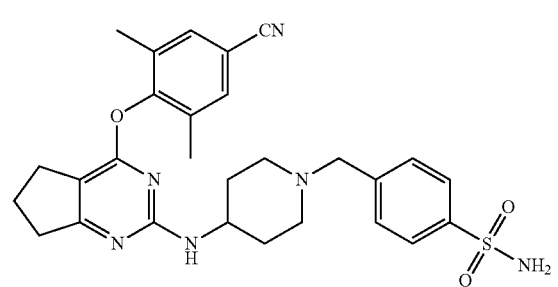

C2
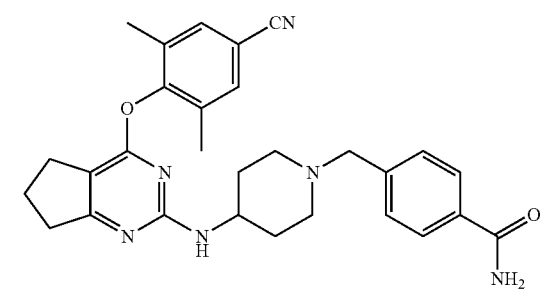

C3
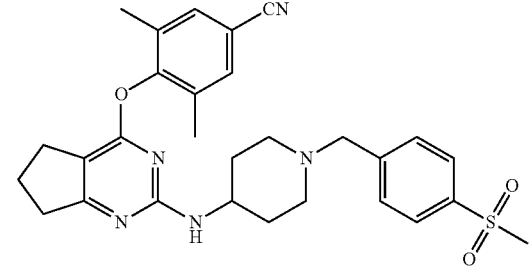

C4
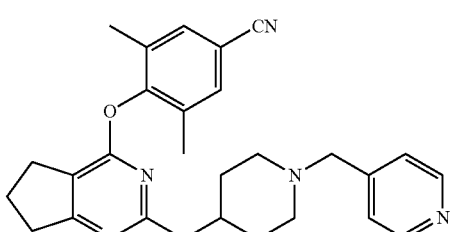

C5
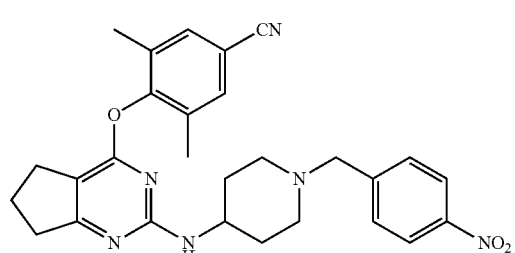

C6
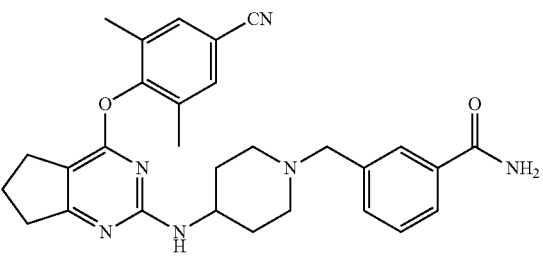

D1
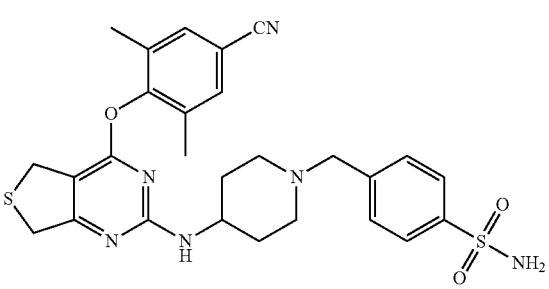

D2
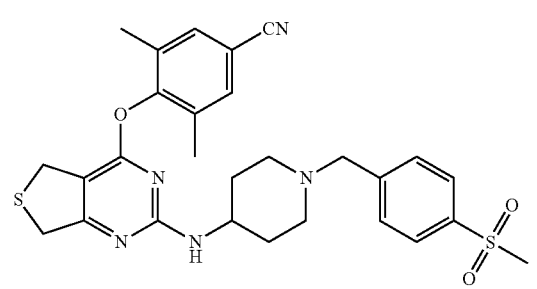

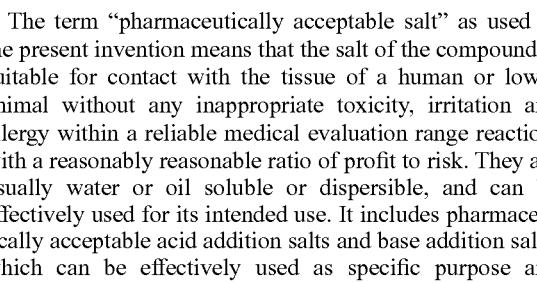

The term "pharmaceutically acceptable salt" as used in the present invention means that the salt of the compound is suitable for contact with the tissue of a human or lower animal without any inappropriate toxicity, irritation and allergy within a reliable medical evaluation range reaction, with a reasonably reasonable ratio of profit to risk. They are usually water or oil soluble or dispersible, and can be effectively used for its intended use. It includes pharmaceutically acceptable acid addition salts and base addition salts, which can be effectively used as specific purpose and compatible with compounds described here. The pharmaceutical acceptable salts are reviewed in S. M. Birge et al. J. Pharm. Sci., 1977, 66, 1-19.

2. Preparation of Five-Membered Non-Aromatic Pyrimidines Derivatives

The preparation method of five-membered non-aromatic pyrimidines derivatives is as follows: Treated the starting material 2,4-dichloro-substituted five-membered non-aromatic pyrimidine 1 with substituted phenol or aniline obtained intermediates 2 via nucleophilic substitution reaction. Then 2 was reacted with N-Boc-4-aminopiperidine got the key intermediates 3, which was directly deprotected with trifluoroacetic acid to yield the key intermediate 4. Finally, 4 was converted into target compounds by nucleophilic substitution with various substitutes of benzyl chloride or benzyl bromide. The synthetic routes are as follows:

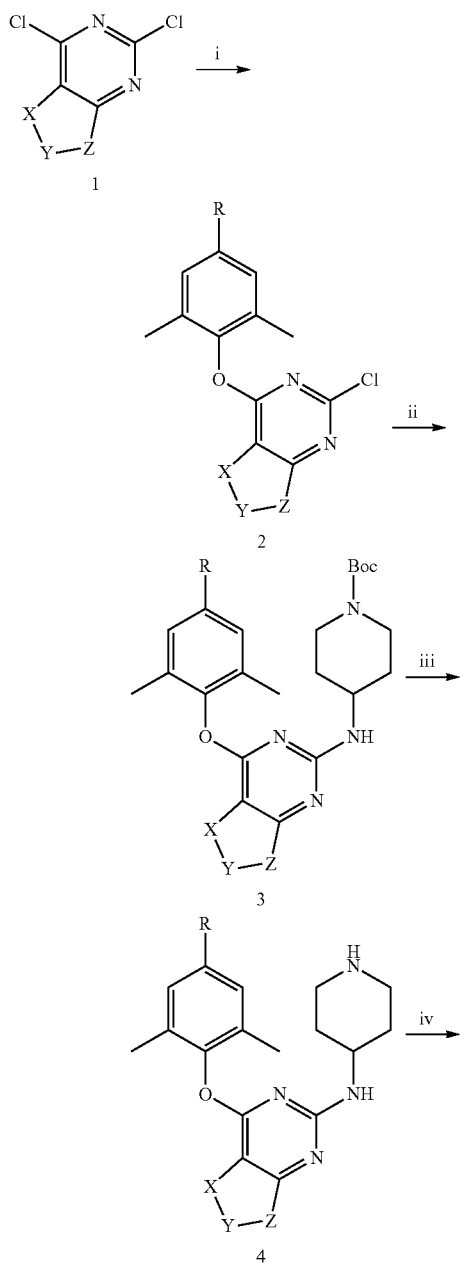

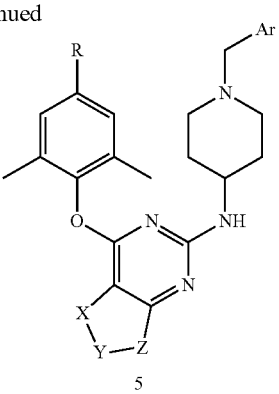

Reagents and conditions: (i) substituted phenol or aniline, DMF, $K_2CO_3$, r.t.; (ii) DMF, $K_2CO_3$, N-Boc-4-aminopiperidine, 100° C.; (iii) TFA, DCM, r.t.; (iv) substituted benzyl bromine, DMF, $K_2CO_3$, r.t.

Wherein, X, Y, Z, R, Ar are the same as general formula I.

Wherein, substituted phenol or aniline is selected from 2,4,6-trimethylphenol, 2, 6-dimethyl-4-cyanophenol, 2,6-dimethyl-4-(E)-cyanovinylphenol, 2,4,6-trimethylaniline, 2, 6-dimethyl-4-cyanoaniline, and 2,6-dimethyl-4-(E)-cyanovinylanilinen.

Wherein, the substituted benzyl chloride/bromide is selected from 1-chloro-2-(chloromethyl)benzene, 1-chloro-3-(chloromethyl)benzene, 1-chloro-4-(chloromethyl) benzene, 1-bromo-2-(bromomethyl)benzene, 1-bromo-3-(bromomethyl)benzene, 1-bromo-4-(bromomethyl) benzene, 1-(chloromethyl)-2-fluorobenzene, 1-(chloromethyl)-3-fluorobenzene, 1-(chloromethyl)-4-fluorobenzene, 1-(bromomethyl)-2,4-difluorobenzene, 1-(bromomethyl)-3,4-difluorobenzene, 2-(chloromethyl)benzonitrile, 3-(chloromethyl)benzonitrile, 4-(chloromethyl)benzonitrile, 1-(chloromethyl)-2-nitrobenzene, 1-(chloromethyl)-3-nitrobenzene, 1-(chloromethyl)-4-nitrobenzene, 1-(chloromethyl)-2-methoxybenzene, 1-(chloromethyl)-3-methoxybenzene, 1-(chloromethyl)-4-methoxybenzene, 1-(bromomethyl)-4-(methylsulfonyl) benzene, 4-(bromomethyl)benzenesulfonamide, 3-(bromomethyl)benzenesulfonamide, 2-(bromomethyl)benzamide, N-(4-(bromomethyl) phenyl)formamide, ethyl 4-(bromomethyl) benzoate, 4-(bromomethyl)benzamide, 3-(bromomethyl)benzamide, N-(4-(bromomethyl)phenyl) methanesulfonamide, etc.

The room temperature of the present invention is from 20 to 30° C.

3. Activity Against Wide-Type and Mutant HIV-1 Strains and Use Thereof

Antiviral potency was evaluated in MT-4 cell cultures infected with WT HIV-1 strain (IIIB) as well as cells infected with a panel of NNRTI-resistant double-mutant strain K103N+Y181C (RES056). Nevirapine (NVP) and etravirine (ETR) were selected as control drugs.

As depicted in Table 1, the results demonstrated that most compounds exhibited nanomolar $EC_{50}$ values towards HIV-1 IIIB. A, A4, B1-4, C1, C3-4, and D2 exhibited more potent activity than that of ETR ($EC_{50}$=5.1 nM), with $EC_{50}$ values ranging from 1.1 to 4.3 nM. Moreover, B2, C1, and C3-4 were demonstrated with lower cytotoxicity ($CC_{50}$>200 µM) and a huge selectivity index (SI) value (ratio of $CC_{50}$/$EC_{50}$) of >100,000. Among all the compounds, C1 proved to be the most potent inhibitor with $EC_{50}$ value of 1.1 nM, being about 4.6-fold potent than ETR. In the case of mutant HIV-1 strain RES056, C1 (EC$_{50}$=25.8 nM, SI>9091) displayed the most effective activity, being more potent than that of ETR (EC$_{50}$=45.4 nM). In addition, A1-2 and B1-4 (EC$_{50}$=28.8-43.6 nM) exhibited comparable activity with ETR against mutant strain RES056. Overall, the results indicate that five-membered non-aromatic pyrimidines compounds hold great promise as potential next-generation anti-HIV drug candidates, and they have great value for further research and development.

Also described here are five-membered non-aromatic pyrimidines derivatives used as HIV-1 NNRTIs, furthermore, these HIV-1 inhibitors will be used as anti-AIDS drugs.

Also described here are pharmaceutical composition comprising five-membered non-aromatic pyrimidines derivatives, and with one or more kind of pharmaceutically acceptable carrier or excipient.

The present invention provides novel five-membered non-aromatic pyrimidines derivatives, their preparation method, anti-HIV-1 activity screening results and their first application in anti-HIV-1 field. The five-membered non-aromatic pyrimidines derivatives of the present invention have been proved to be useful as HIV-1 inhibitors and have high application value. In particular, the inhibitors could be used as anti-AIDS drugs.

EXAMPLES

Selected examples are listed as follows, the invention includes these compounds disclosed herein but not confined to them.

The synthetic routes involved in the examples are as follows:

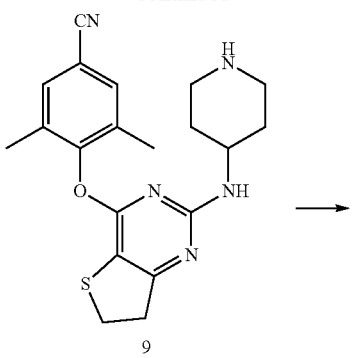

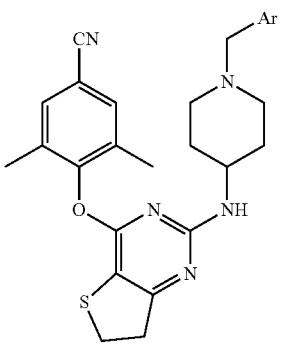

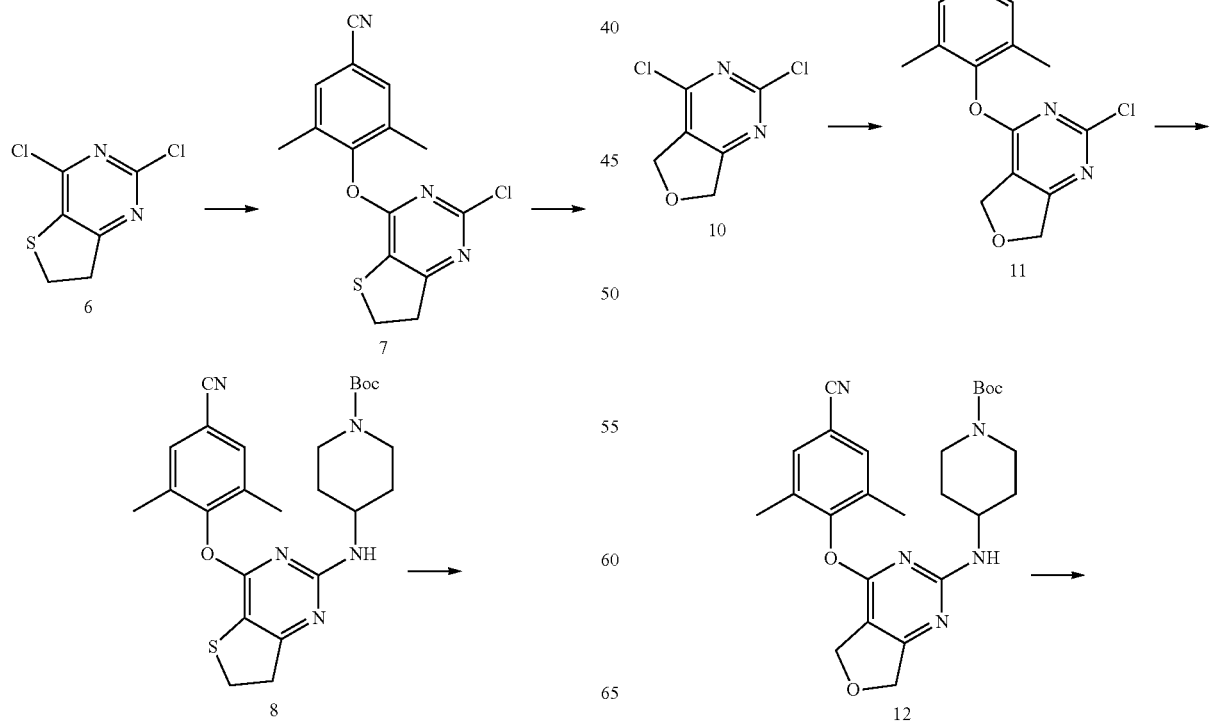

11
-continued
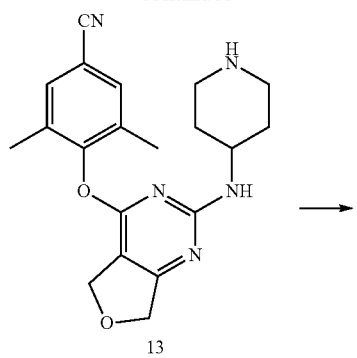
13
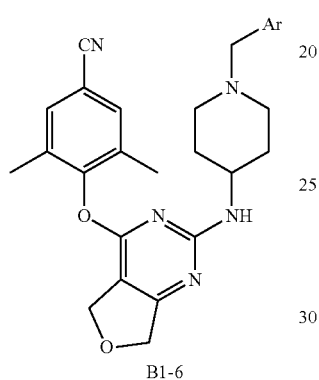
B1-6
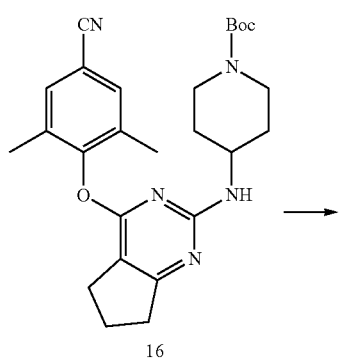
16
12
-continued
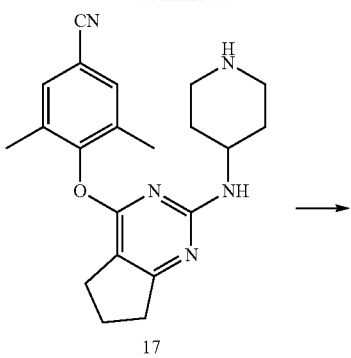
17
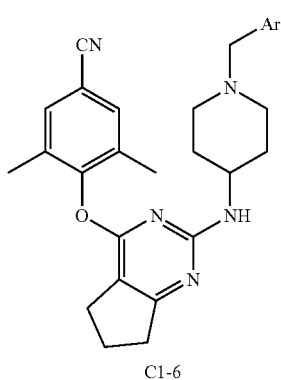
C1-6
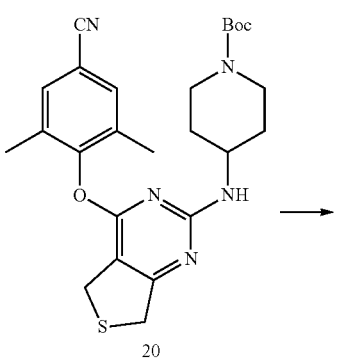
20
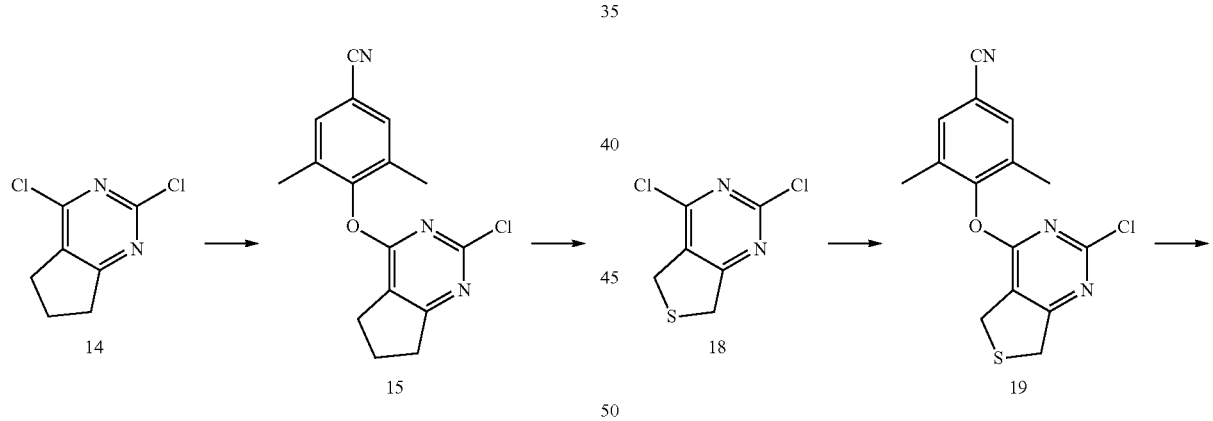

13

-continued

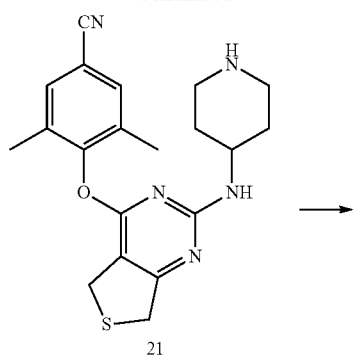

21

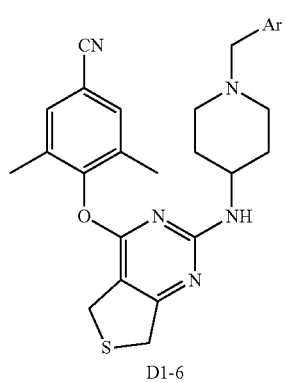

D1-6

Example 1: 4-((2-chloro-6,7-dihydrothieno[3,2-d]pyrimidin-4-yl)oxy)-3,5-dimethylbenzonitrile (7)

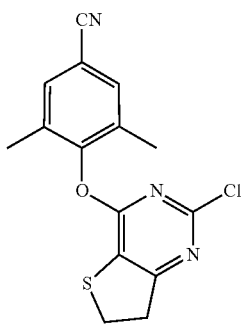

7

A reaction mixture of 4-hydroxy-3,5-dimethylbenzonitrile (1.5 g, 10 mmol) and potassium carbonate (1.7 g, 12 mmol) in 30 mL of DMF was stirred at 25° C. for 15 min, and then 2,4-dichloro-6,7-dihydrothieno[3,2-d]pyrimidine (2.1 g, 10 mmol) was added to it. Stirring was continued for an additional 2.0 h (monitored by TLC), then the mixture was poured into ice water, the precipitated white solid was collected by filtration, washed with cold water, and recrystallized in DMF-H$_2$O to provide the desired product 7 as white solid, 86% yield. mp: 272-274° C. $^1$H NMR (400 MHz, DMSO-d$_6$) δ 7.67 (s, 2H, C$_3$,C$_5$-Ph-H), 3.37-3.35 (m, 2H), 3.14 (t, J=8.2 Hz, 2H, S—CH$_2$), 2.06 (s, 6H). HRMS: m/z 318.0411 [M+1]$^+$. C$_{15}$H$_{12}$ClN$_3$OS (317.0390).

14

Example 2: 3,5-dimethyl-4-((2-(piperidin-4-ylamino)-6,7-dihydrothieno[3,2-d]pyrimidin-4-yl)oxy)benzonitrile (9)

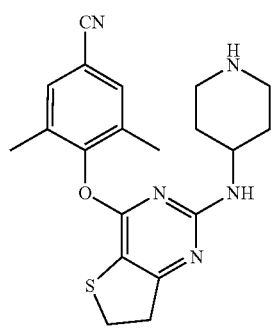

9

A solution of 7 (1.0 g, 3.17 mmol), tert-butyl 4-aminopiperidine-1-carboxylate (0.83 g, 3.80 mmol), and anhydrous K$_2$CO$_3$ (0.87 g, 6.33 mmol) in 5 mL of DMF was heated at 100° C. for 10 h. After completion (monitored by TLC), the mixture was cooled to room temperature and 50 mL of ice water was added. The reaction mixture was continuously stirred for another 30 min and the resulting precipitate was collected and dried to give the intermediate 8, which was used directly without purification. To a solution of 8 (1.26 g, 2.53 mmol) in dichloromethane (DCM) (4 mL) was added trifluoroacetic acid (TFA) (2.22 mL, 30 mmol) at room temperature. After the mixture was stirred for 4 h (monitored by TLC), it was alkalized to pH 9 with saturated sodium bicarbonate solution and washed with saturated salt water (15 mL). The aqueous phase was extracted with DCM (3×5 mL). The combined organic phase was dried over Na$_2$SO$_4$. The filtrate was concentrated and purified by column chromatography on silica gel to get 9 as a white solid with 58% yield, mp: 135-137° C. $^1$H NMR (400 MHz, DMSO-d$_6$) δ 7.67 (s, 2H, C$_3$,C$_5$-Ph-H), 7.09 (s, 1H, NH), 3.36-3.35 (m, 3H), 3.13 (t, J=8.0 Hz, 2H, S—CH$_2$), 2.71-2.62 (m, 2H), 2.06 (s, 6H), 1.83-1.45 (m, 6H). HRMS: m/z 382.1692 [M+1]$^+$. C$_{20}$H$_{23}$N$_5$OS (381.1623).

Example 3: Preparation of A1-A6

Compounds 9 (0.5 mmol) was dissolved in anhydrous DMF (5 mL) in the presence of anhydrous K$_2$CO$_3$ (0.14 g, 1.0 mmol), followed by addition of appropriate substituted benzyl chloride (bromine) (0.6 mmol). The reaction mixture was stirred at room temperature for 6-8 h. The solvent was removed under reduced pressure, and then water (20 mL) was added. Extracted with ethyl acetate (3×10 mL), and the organic phase was washed with saturated sodium chloride (10 mL), then dried over anhydrous Na$_2$SO$_4$ to give the corresponding crude product, which was purified by flash column chromatography and recrystallized from Ethyl acetate (EA)/petroleum ether (PE) to afford the target compounds A1-A6.

4-((4-((4-(4-cyano-2,6-dimethylphenoxy)-6,7-dihydrothieno[3,2-d]pyrimidin-2-yl)amino)piperidin-1-yl)methyl)benzenesulfonamide (A1)

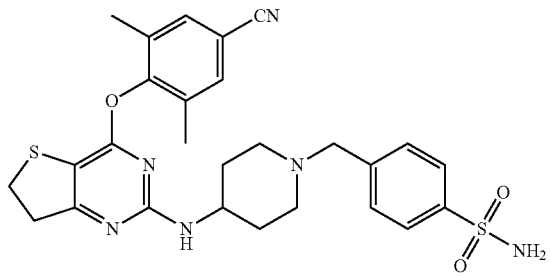 [SMILES: Cc1cc(C#N)cc(C)c1Oc1nc(NC2CCN(Cc3ccc(S(N)(=O)=O)cc3)CC2)nc2c1SCC2]

Starting with 9 and 4-(bromomethyl)benzenesulfonamide to afford A1 as a white solid. Yield: 58%, mp: 201-203° C.

$^1$H NMR (400 MHz, DMSO-$d_6$) δ 7.77 (d, J=8.0 Hz, 2H, $C_3$,C-Ph'-H), 7.67 (s, 2H, $C_3$,$C_5$-Ph"-H), 7.45 (d, J=8.0 Hz, 2H, $C_2$,$C_6$-Ph'-H), 7.31 (s, 2H, SO$_2$NH$_2$), 7.09 (s, 1H, NH), 3.45 (s, 2H, N—CH$_2$), 3.37-3.35 (m, 3H), 3.14 (t, J=8.2 Hz, 2H, S—CH$_2$), 2.71-2.60 (m, 2H), 2.06 (s, 6H), 1.80-1.20 (m, 6H). $^{13}$C NMR (100 MHz, DMSO-$d_6$) δ 162.0, 160.6, 143.3, 143.1, 133.1, 129.4, 126.0, 119.1, 108.6, 61.9, 52.6, 31.5, 29.3, 16.2. HRMS: m/z 551.1890 [M+1]$^+$. $C_{27}H_{30}N_6O_3S_2$ (550.1821).

4-((4-((4-(4-cyano-2,6-dimethylphenoxy)-6,7-dihydrothieno[3,2-d]pyrimidin-2-yl)amino)piperidin-1-yl)methyl)benzamide (A2)

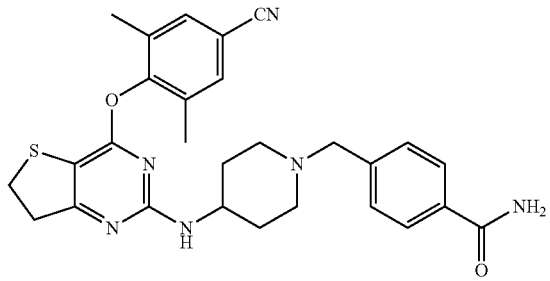

Starting with 9 and 4-(chloromethyl)benzamide to afford A2 as a white solid. Yield: 67%, mp: 245-248° C.

$^1$H NMR (400 MHz, DMSO-$d_6$) δ 7.92 (s, 1H), 7.82 (d, J=8.0 Hz, 2H, $C_3$,$C_5$-Ph'-H), 7.67 (s, 2H, $C_3$,$C_5$-Ph"-H), 7.34-7.32 (m, 3H), 6.95 (s, 1H, NH), 3.43 (s, 2H, N—CH$_2$), 3.39-3.30 (m, 3H), 3.14 (t, J=8.1 Hz, 2H, S—CH$_2$), 2.67 (s, 2H), 2.06 (s, 6H), 1.78-1.19 (m, 6H). $^{13}$C NMR (101 MHz, DMSO-$d_6$) δ 168.2, 160.6, 142.5, 133.4, 133.1, 132.6, 128.8, 127.8, 108.6, 62.2, 52.6, 36.9, 31.5, 29.3, 16.2. HRMS: m/z 515.2219 [M+1]$^+$. $C_{28}H_{30}N_6O_2S$ (514.2151).

3,5-dimethyl-4-((2-((1-(4-(methylsulfonyl)benzyl)piperidin-4-yl)amino)-6,7-dihydrothieno[3,2-d]pyrimidin-4-yl)oxy)benzonitrile (A3)

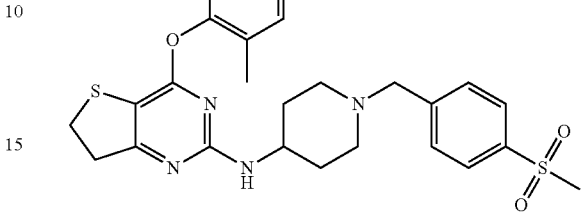

Starting with 9 and 1-(bromomethyl)-4-(methylsulfonyl)benzene to afford A3 as a white solid. Yield: 70%, mp: 142-144° C.

$^1$H NMR (400 MHz, DMSO-$d_6$) δ 7.87 (d, J=7.9 Hz, 2H, $C_3$,$C_5$-Ph'-H), 7.67 (s, 2H, $C_3$,$C_5$-Ph"-H), 7.54 (d, J=8.0 Hz, 2H, $C_2$,$C_6$-Ph'-H), 7.10 (s, 1H, NH), 3.50 (s, 2H, N—CH$_2$), 3.40-3.29 (m, 3H), 3.20 (s, 3H, SO$_2$CH$_3$), 3.15 (t, J=8.0 Hz, 2H, S—CH$_2$), 2.67 (s, 2H), 2.07 (s, 6H), 1.77-1.21 (m, 6H). $^{13}$C NMR (100 MHz, DMSO-$d_6$) δ 160.6, 145.4, 139.8, 133.1, 132.7, 129.7, 127.4, 119.1, 108.6, 61.8, 52.6, 44.0, 31.6, 29.3, 16.2. HRMS: m/z 550.1946 [M+1]$^+$. $C_{28}H_{31}N_5O_3S_2$ (549.1868).

3,5-dimethyl-4-((2-((1-(pyridin-4-ylmethyl)piperidin-4-yl)amino)-6,7-dihydrothieno[3,2-d]pyrimidin-4-yl)oxy)benzonitrile (A4)

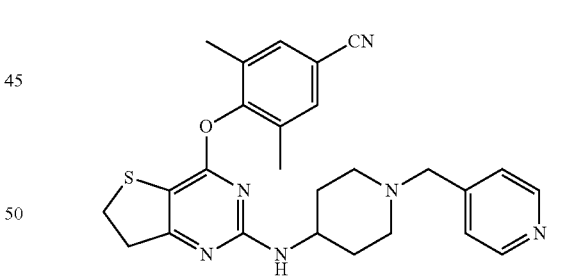

Starting with 9 and 4-(chloromethyl)pyridine to afford A4 as a white solid. Yield: 54%, mp: 140-142° C.

$^1$H NMR (400 MHz, DMSO-$d_6$) δ 8.49 (d, J=5.4 Hz, 2H, $C_3$,$C_5$-Ph'-H), 7.66 (s, 2H, $C_3$,$C_5$-Ph"-H), 7.28 (d, J=5.1 Hz, 2H, $C_2$,$C_6$-Ph'), 7.07 (s, 1H, NH), 3.43 (s, 2H, N—CH$_2$), 3.39-3.25 (m, 3H), 3.15 (t, J=8.1 Hz, 2H, S—CH$_2$), 2.67 (s, 2H), 2.07 (s, 6H), 1.79-1.23 (m, 6H). $^{13}$C NMR (100 MHz, DMSO-$d_6$) δ 162.0, 160.6, 153.9, 149.9, 148.1, 133.1, 132.6, 124.1, 108.6, 61.2, 52.6, 36.9, 31.5, 29.3, 16.2. HRMS: m/z 473.2118 [M+1]$^+$. $C_{26}H_{28}N_6OS$ (472.2045).

3,5-dimethyl-4-((2-((1-(4-nitrobenzyl)piperidin-4-yl)amino)-6,7-dihydrothieno[3,2-d]pyrimidin-4-yl)oxy)benzonitrile (A5)

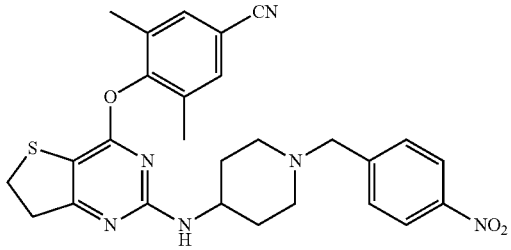

Starting with 9 and 1-(chloromethyl)-4-nitrobenzene to afford A5 as a white solid. Yield: 62%, mp: 158-160° C.

$^1$H NMR (400 MHz, DMSO-$d_6$) δ 8.19 (d, J=8.3 Hz, 2H, $C_3$,$C_5$-Ph'-H), 7.66 (s, 2H, $C_3$,$C_5$-Ph"-H), 7.55 (d, J=8.3 Hz, 2H, $C_2$,$C_6$-Ph'-H), 7.07 (s, 1H, NH), 3.54 (s, 2H, N—$CH_2$), 3.39-3.25 (m, 3H), 3.15 (t, J=8.0 Hz, 2H, S—$CH_2$), 2.68 (s, 2H), 2.07 (s, 6H), 1.82-1.20 (m, 6H). $^{13}$C NMR (100 MHz, DMSO-$d_6$) δ 162.0, 160.6, 147.5, 146.9, 133.1, 132.7, 130.0, 123.8, 119.0, 108.6, 61.6, 52.6, 39.4, 36.9, 31.6, 29.3, 16.2. HRMS: m/z 517.2016 [M+1]$^+$. $C_{27}H_{28}N_6O_3S$ (516.1944).

3-((4-((4-(4-cyano-2,6-dimethylphenoxy)-6,7-dihydrothieno[3,2-d]pyrimidin-2-yl)amino)piperidin-1-yl)methyl)benzamide (A6)

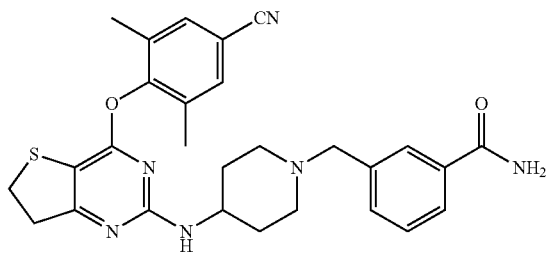

Starting with 9 and 3-(chloromethyl)benzamide to afford A6 as a white solid. Yield: 47%, mp: 215-217° C.

$^1$H NMR (400 MHz, DMSO-$d_6$) δ 7.95 (s, 1H, $C_2$-Ph'-H), 7.75 (dd, J=11.0, 3.9 Hz, 2H, $C_5$,$C_6$-Ph'-H), 7.66 (s, 2H, $C_3$,$C_5$-Ph"-H), 7.46-7.25 (m, 3H), 7.06 (s, 1H, NH), 3.43 (s, 2H, N—$CH_2$), 3.39-3.25 (m, 3H), 3.15 (t, J=8.1 Hz, 2H, S—$CH_2$), 2.68 (s, 2H), 2.07 (s, 6H), 1.81-1.24 (m, 6H). $^{13}$C NMR (100 MHz, DMSO-$d_6$) δ 168.4, 162.0, 160.6, 139.2, 134.6, 133.1, 132.7, 132.0, 128.4, 126.4, 119.0, 108.6, 62.4, 52.6, 36.9, 31.6, 29.3, 16.2. HRMS: m/z 515.2229 [M+1]$^+$. $C_{28}H_{30}N_6O_2S$ (514.2151).

Example 4: 4-((2-chloro-5,7-dihydrofuro[3,4-d]pyrimidin-4-yl)oxy)-3,5-dimethylbenzonitrile (11)

The synthetic method was similar to that described for 7, with the difference that the starting material was 2,4-dichloro-5,7-dihydrofuro[3,4-d]pyrimidine (10). White solid, Yield: 88%, mp: 180-183° C. $^1$H NMR (400 MHz, DMSO-$d_6$) δ 7.69 (s, 2H, $C_3$,$C_5$-Ph-H), 4.97 (s, 2H, $C_5$-dihydrofuropyrimidine), 4.80 (s, 2H, $C_7$-dihydrofuropyrimidine), 2.10 (s, 6H). HRMS: m/z 302.0687 [M+1]$^+$. $C_{15}H_{12}ClN_3O_2$ (301.0618).

Example 5: 3,5-dimethyl-4-((2-(piperidin-4-ylamino)-5,7-dihydrofuro[3,4-d]pyrimidin-4-yl)oxy)benzonitrile (13)

The synthetic method was similar to that described for 9, with the difference that the starting material was 4-((2-chloro-5,7-dihydrofuro[3,4-d]pyrimidin-4-yl)oxy)-3,5-dimethylbenzonitrile (11). White solid, Yield: 61%, mp: 122-124° C. H NMR (400 MHz, DMSO-$d_6$) δ 7.67 (s, 2H, $C_3$,$C_5$-Ph-H), 7.08 (s, 1H, NH), 4.96 (s, 2H, $C_5$-dihydrofuropyrimidine), 4.77 (s, 2H, $C_7$-dihydrofuropyrimidine), 3.63-3.61 (m, 1H), 2.67 (s, 2H), 2.09 (s, 6H), 1.97-1.32 (m, 6H). HRMS: m/z 366.1843 [M+1]$^+$. $C_2H_{23}N_5O_2$ (365.1852).

Example 3: Preparation of B1-B6

The synthetic method was similar to that described for A1-A6, with the difference that the starting material was compound 13.

4-((4-((4-(4-cyano-2,6-dimethylphenoxy)-5,7-dihydrofuro[3,4-d]pyrimidin-2-yl)amino)piperidin-1-yl)methyl)benzenesulfonamide (B1)

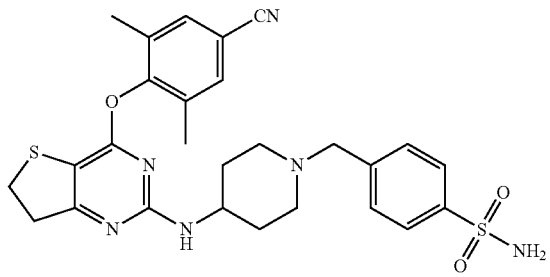

Starting with 13 and 4-(bromomethyl)benzenesulfonamide to afford B1 as a white solid. Yield: 66%, mp: 191-193° C.

$^1$H NMR (400 MHz, DMSO-$d_6$) δ 7.77 (d, J=8.0 Hz, 2H, $C_3$,$C_5$-Ph'-H), 7.67 (s, 2H, $C_3$,$C_5$-Ph"-H), 7.45 (d, J=8.0 Hz, 2H, $C_2$,$C_6$-Ph'-H), 7.31 (s, 2H, $SO_2NH_2$), 7.08 (s, 1H, NH), 4.96 (s, 2H, $C_5$-dihydrofuropyrimidine), 4.77 (s, 2H, $C_7$-dihydrofuropyrimidine), 3.63 (s, 1H), 3.47 (s, 2H, N—$CH_2$), 2.69 (s, 2H), 2.09 (s, 6H), 1.94-1.18 (m, 6H). $^{13}$C NMR (101 MHz, DMSO-$d_6$) δ 162.9, 162.0, 143.3, 143.1, 133.1, 129.4, 126.9, 126.2, 126.0, 119.0, 61.9, 52.6, 31.5, 16.2. HRMS: m/z 535.2126 [M+1]$^+$. $C_{27}H_{30}N_6O_4S$ (534.2049).

4-((4-((4-(4-cyano-2,6-dimethylphenoxy)-5,7-dihydrofuro[3,4-d]pyrimidin-2-yl)amino)piperidin-1-yl)methyl)benzamide (B2)

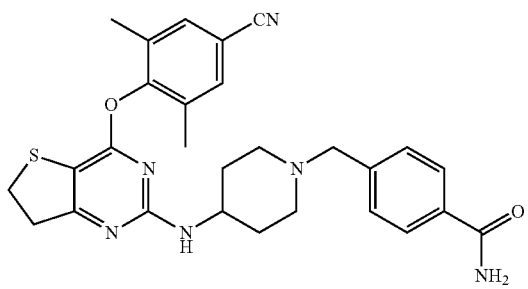 [SMILES: Cc1cc(C#N)cc(C)c1Oc1nc(NC2CCN(Cc3ccc(C(N)=O)cc3)CC2)nc2c1SCC2]

Starting with 13 and 4-(chloromethyl)benzamide to afford B2 as a white solid. Yield: 57%, mp: 238-240° C.

$^1$H NMR (400 MHz, DMSO-$d_6$) δ 7.85 (s, 2H, $CONH_2$), 7.75 (d, J=7.9 Hz, 2H, $C_3$,$C_5$-Ph'-H), 7.60 (s, 2H, $C_3$,$C_5$-Ph"-H), 7.26 (d, J=8.1 Hz, 2H, $C_2$,$C_6$-Ph'-H), 7.00 (s, 1H, NH), 4.89 (s, 2H, $C_5$-dihydrofuropyrimidine), 4.70 (s, 2H, $C_7$-dihydrofuropyrimidine), 3.60 (s, 1H), 3.42 (s, 2H, N—$CH_2$), 2.74-2.53 (m, 2H), 2.02 (s, 6H), 1.93-1.11 (m, 6H). $^{13}$C NMR (100 MHz, DMSO-$d_6$) δ 168.2, 162.9, 162.5, 142.5, 133.4, 133.1, 132.5, 128.8, 127.8, 119.0, 108.7, 62.2, 52.6, 31.6, 16.2. HRMS: m/z 499.2457 [M+1]$^+$. $C_{28}H_{30}N_6O_3$ (498.2397).

3,5-dimethyl-4-((2-((1-(4-(methylsulfonyl)benzyl)piperidin-4-yl)amino)-5,7-dihydrofuro[3,4-d]pyrimidin-4-yl)oxy)benzonitrile (B3)

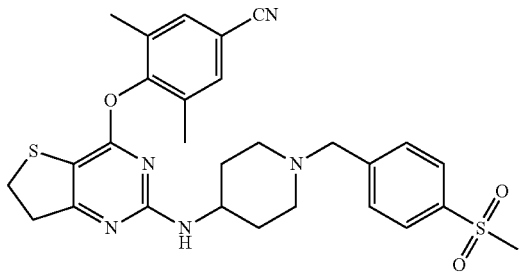 [SMILES: Cc1cc(C#N)cc(C)c1Oc1nc(NC2CCN(Cc3ccc(S(C)(=O)=O)cc3)CC2)nc2c1SCC2]

Starting with 13 and 1-(bromomethyl)-4-(methylsulfonyl)benzene to afford B3 as a white solid. Yield: 72%, mp: 209-211° C.

$^1$H NMR (400 MHz, DMSO-$d_6$) δ 7.87 (d, J=8.0 Hz, 2H, $C_3$,$C_5$-Ph'-H), 7.67 (s, 2H, $C_3$,$C_5$-Ph"-H), 7.54 (d, J=8.0 Hz, 2H, $C_2$,$C_6$-Ph'-H), 7.08 (s, 1H, NH), 4.96 (s, 2H, $C_5$-dihydrofuropyrimidine), 4.77 (s, 2H, $C_7$-dihydrofuropyrimidine), 3.68 (s, 1H), 3.51 (s, 2H, N—$CH_2$), 3.20 (s, 3H, $SO_2CH_3$), 2.76-2.62 (m, 2H), 2.09 (s, 6H), 1.90-1.15 (m, 6H). $^{13}$C NMR (101 MHz, DMSO-$d_6$) δ 162.9, 162.5, 145.4, 139.8, 133.1, 129.7, 127.4, 108.7, 69.3, 61.8, 52.6, 44.0, 31.5, 16.2. HRMS: m/z 534.2173 [M+1]$^+$. $C_{28}H_{31}N_5O_4S$ (533.2097).

3,5-dimethyl-4-((2-((1-(pyridin-4-ylmethyl)piperidin-4-yl)amino)-5,7-dihydrofuro[3,4-d]pyrimidin-4-yl)oxy)benzonitrile (B4)

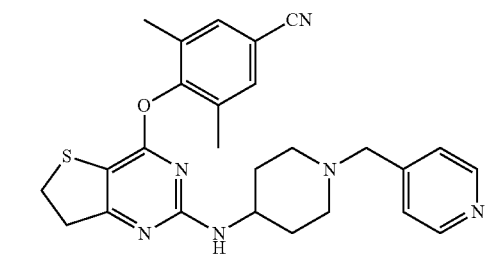 [SMILES: Cc1cc(C#N)cc(C)c1Oc1nc(NC2CCN(Cc3ccncc3)CC2)nc2c1SCC2]

Starting with 13 and 4-(chloromethyl)pyridine to afford B4 as a white solid. Yield: 73%, mp: 155-157° C.

$^1$H NMR (400 MHz, DMSO-$d_6$) δ 8.50 (d, J=5.9 Hz, 2H, $C_3$,$C_5$-Ph'-H), 7.67 (s, 2H, $C_3$,$C_5$-Ph"-H), 7.28 (d, J=5.1 Hz, 2H, $C_2$,$C_6$-Ph'-H), 7.09 (s, 1H, NH), 4.96 (s, 2H, $C_5$-dihydrofuropyrimidine), 4.77 (s, 2H, $C_7$-dihydrofuropyrimidine), 3.68 (s, 1H), 3.45 (s, 2H, N—$CH_2$), 2.77-2.59 (m, 2H), 2.09 (s, 6H), 1.91-1.22 (m, 6H). $^{13}$C NMR (100 MHz, DMSO-$d_6$) δ 162.9, 149.9, 148.1, 133.1, 124.1, 108.7, 69.4, 61.2, 52.6, 31.4, 16.2. HRMS: m/z 457.2345 [M+1]$^+$. $C_{26}H_{28}N_6O_2$ (456.2274).

3,5-dimethyl-4-((2-((1-(4-nitrobenzyl)piperidin-4-yl)amino)-5,7-dihydrofuro[3,4-d]pyrimidin-4-yl)oxy)benzonitrile (B5)

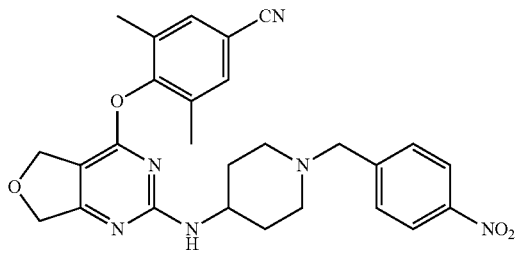 [SMILES: Cc1cc(C#N)cc(C)c1Oc1nc(NC2CCN(Cc3ccc([N+](=O)[O-])cc3)CC2)nc2c1COC2]

Starting with 13 and 1-(chloromethyl)-4-nitrobenzene afford B5 as a white solid. Yield: 61%, mp: 199-201° C.

$^1$H NMR (400 MHz, DMSO-d$_6$) δ 8.12 (d, J=8.6 Hz, 2H, C$_3$,C$_5$-Ph'-H), 7.60 (s, 2H, C$_3$,C$_5$-Ph"-H), 7.49 (d, J=8.4 Hz, 2H, C$_2$,C$_6$-Ph'-H), 7.02 (s, 1H, NH), 4.89 (s, 2H, C$_5$-dihydrofuropyrimidine), 4.70 (s, 2H, C$_7$-dihydrofuropyrimidine), 3.61 (s, 1H), 3.47 (s, 2H, N—CH$_2$), 2.63 (s, 2H), 2.02 (s, 6H), 1.80-1.14 (m, 6H). $^{13}$C NMR (100 MHz, DMSO-d$_6$) δ 162.9, 146.9, 133.1, 130.0, 123.8, 61.6, 52.6, 39.6, 39.4, 31.5, 16.2. HRMS: m/z 501.2247 [M+1]$^+$. C$_{27}$H$_{28}$N$_6$O$_4$ (500.2172).

3-((4-((4-(4-cyano-2,6-dimethylphenoxy)-5,7-dihydrofuro[3,4-d]pyrimidin-2-yl)amino)piperidin-1-yl)methyl)benzamide (B6)

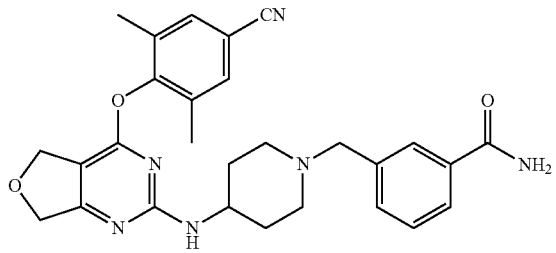 [SMILES: Cc1cc(C#N)cc(C)c1Oc1nc(NC2CCN(Cc3cccc(C(N)=O)c3)CC2)nc2c1COC2]

Starting with 13 and 1-(chloromethyl)-4-nitrobenzene afford B6 as a white solid. Yield: 43%, mp: 225-227° C.

$^1$H NMR (400 MHz, DMSO-d$_6$) δ 7.88 (s, 2H, CONH$_2$), 7.70 (s, 1H, C$_2$-Ph'-H), 7.69-7.66 (m, 1H), 7.60 (s, 2H, C$_3$,C$_5$-Ph"-H), 7.35-7.30 (m, 2H, C$_2$,C$_6$-Ph'-H), 7.01 (s, 1H, NH), 4.89 (s, 2H, C$_5$-dihydrofuropyrimidine), 4.70 (s, 2H, C$_7$-dihydrofuropyrimidine), 3.60 (s, 1H), 3.36 (s, 2H, N—CH$_2$), 2.63 (s, 2H), 2.02 (s, 6H), 1.92-1.16 (m, 6H). $^{13}$C NMR (101 MHz, DMSO-d$_6$) δ 168.4, 163.0, 162.5, 139.2, 134.6, 133.1, 132.0, 128.4, 126.4, 119.0, 108.7, 69.4, 62.4, 55.3, 52.6, 39.6, 31.6, 16.2. HRMS: m/z 499.2456 [M+1]$^+$. C$_2$H$_{30}$N$_6$O$_3$ (498.2379).

Example 7: 4-((2-chloro-6,7-dihydro-5H-cyclopenta[d]pyrimidin-4-yl)oxy)-3,5-dimethylbenzonitrile (15)

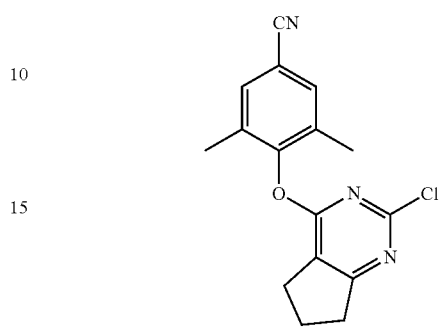

The synthetic method was similar to that described for 7, with the difference that the starting material was 2,4-dichloro-6,7-dihydro-5H-cyclopenta[d]pyrimidine (14). White solid. Yield: 97%, mp: 254-256° C. $^1$H NMR (400 MHz, DMSO-d$_6$) δ 7.73 (s, 2H, C$_3$,C$_5$-Ph-H), 3.04 (t, J=7.8 Hz, 2H), 2.92 (t, J=7.7 Hz, 2H), 2.13 (p, J=7.7 Hz, 2H), 2.09 (s, 6H). HRMS: m/z 300.0895 [M+1]$^+$. C$_{16}$H$_4$ClN$_3$O (299.0825).

Example 8: 3,5-dimethyl-4-((2-(piperidin-4-ylamino)-6,7-dihydro-5H-cyclopenta[d]pyrimidin-4-yl)oxy)benzonitrile (17)

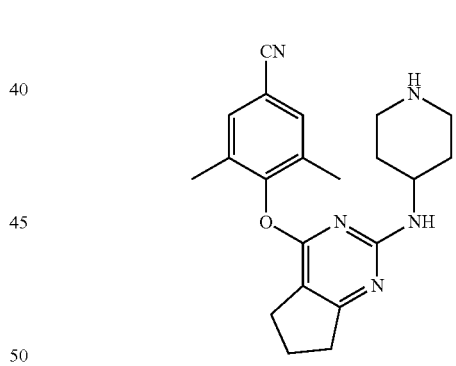

The synthetic method was similar to that described for 9, with the difference that the starting material was 15. White solid. Yield: 67%, mp: 135-137° C. H NMR (400 MHz, DMSO-d$_6$) δ 7.64 (s, 2H, C$_3$,C$_5$-Ph-H), 6.90 (s, 1H, NH), 3.65 (s, 1H), 2.76-2.72 (m, 4H), 2.69-2.59 (m, 2H), 2.07 (s, 6H), 2.02-1.97 (m, 2H), 1.81-1.21 (m, 6H). HRMS: m/z 364.2132 [M+1]$^+$. C$_{21}$H$_{25}$N$_5$O (363.2059).

Example 9: Preparation of C1-C6

The synthetic method was similar to that described for A1-A6, with the difference that the starting material was compound 17.

4-((4-((4-(4-cyano-2,6-dimethylphenoxy)-6,7-dihydro-5H-cyclopenta[d]pyrimidin-2-yl)amino)piperidin-1-yl)methyl)benzenesulfonamide (C1)

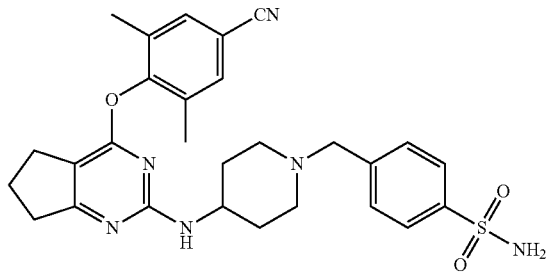 [SMILES: Cc1cc(C#N)cc(C)c1Oc1nc(NC2CCN(Cc3ccc(S(N)(=O)=O)cc3)CC2)nc2c1CCC2]

Starting with 17 and 4-(bromomethyl)benzenesulfonamide to afford C1 as a white solid. Yield: 80%, mp: 207-209° C.

$^1$H NMR (400 MHz, DMSO-$d_6$) δ 7.77 (d, J=8.3 Hz, 2H, C$_3$,C$_5$-Ph'-H), 7.64 (s, 2H, C$_3$,C$_5$-Ph"-H), 7.45 (d, J=8.1 Hz, 2H, C$_2$,C$_6$-Ph'-H), 7.30 (s, 2H, SO$_2$NH$_2$), 6.90 (s, 1H, NH), 3.65 (s, 1H), 3.45 (s, 2H), 2.76 (dt, J=22.3, 7.7 Hz, 4H), 2.69-2.59 (m, 2H), 2.07 (s, 6H), 2.02 (d, J=7.4 Hz, 2H), 1.81-1.21 (m, 6H). $^{13}$C NMR (100 MHz, DMSO-$d_6$) δ 162.0, 143.3, 143.1, 133.1, 132.6, 129.4, 126.0, 119.1, 108.3, 62.0, 52.6, 39.6, 31.6, 25.9, 22.0, 16.3. HRMS: m/z 533.2330 [M+1]$^+$. C$_{28}$H$_{32}$N$_6$O$_3$S (532.2257).

4-((4-((4-(4-cyano-2,6-dimethylphenoxy)-6,7-dihydro-5H-cyclopenta[d]pyrimidin-2-yl)amino)piperidin-1-yl)methyl)benzamide (C2)

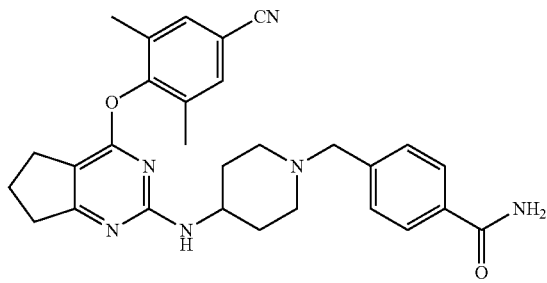 [SMILES: Cc1cc(C#N)cc(C)c1Oc1nc(NC2CCN(Cc3ccc(C(N)=O)cc3)CC2)nc2c1CCC2]

Starting with 17 and 4-(chloromethyl)benzamide to afford C2 as a white solid. Yield: 68%, mp: 225-227° C.

$^1$H NMR (400 MHz, DMSO-$d_6$) δ 7.90 (s, 2H, CONH$_2$), 7.81 (d, J=7.9 Hz, 2H, C$_3$,C$_5$-Ph'-H), 7.64 (s, 2H, C$_3$,C$_5$-Ph"-H), 7.32 (d, J=8.0 Hz, 2H, C$_2$,C$_6$-Ph'-H), 6.89 (s, 1H, NH), 3.65 (s, 1H), 3.48-3.36 (m, 2H), 2.76 (dt, J=22.1, 7.7 Hz, 4H), 2.70-2.58 (m, 2H), 2.07 (s, 6H), 2.02 (d, J=7.4 Hz, 2H), 1.70-1.23 (m, 6H). $^{13}$C NMR (100 MHz, DMSO-$d_6$) δ 168.2, 162.0, 143.1, 142.5, 133.4, 133.1, 129.5, 128.8, 127.8, 119.5, 108.7, 62.2, 52.7, 39.0, 31.2, 25.9, 22.0, 16.3. HRMS: m/z 497.2657 [M+1]$^+$. C$_{29}$H$_{32}$N$_6$O$_2$ (496.2587).

3,5-dimethyl-4-((2-((1-(4-(methylsulfonyl)benzyl)piperidin-4-yl)amino)-6,7-dihydro-5H-cyclopenta[d]pyrimidin-4-yl)oxy)benzonitrile (C3)

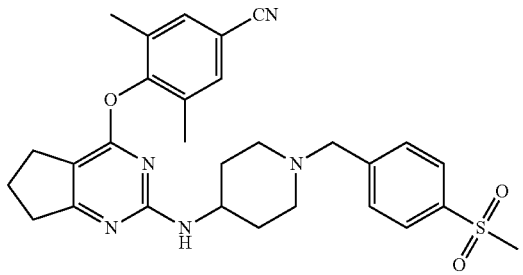 [SMILES: Cc1cc(C#N)cc(C)c1Oc1nc(NC2CCN(Cc3ccc(S(C)(=O)=O)cc3)CC2)nc2c1CCC2]

Starting with 17 and 1-(bromomethyl)-4-(methylsulfonyl)benzene to afford C3 as a white solid. Yield: 69%, mp: 170-172° C.

$^1$H NMR (400 MHz, DMSO-$d_6$) δ 7.89-7.85 (m, 2H), 7.65 (s, 2H, C$_3$,C$_5$-Ph"-H), 7.54 (d, J=8.1 Hz, 2H), 6.80 (s, 1H, NH), 3.66 (s, 1H), 3.50 (s, 2H, N—CH$_2$), 2.89 (s, 3H), 2.78 (dd, J=14.7, 7.3 Hz, 4H), 2.71-2.61 (m, 2H), 2.07 (s, 6H), 2.03 (d, J=7.5 Hz, 2H), 1.81-1.23 (m, 6H). $^3$C NMR (100 MHz, DMSO-$d_6$) δ 162.7, 162.0, 145.4, 139.8, 133.1, 132.6, 129.7, 127.4, 127.3, 108.3, 62.6, 61.9, 52.6, 44.1, 44.0, 36.2, 31.6, 31.2, 25.9, 22.0, 16.3. HRMS: m/z 532.2377 [M+1]$^+$. C$_{29}$H$_{33}$N$_5$O$_3$S (531.2304).

3,5-dimethyl-4-((2-((1-(pyridin-4-ylmethyl)piperidin-4-yl)amino)-6,7-dihydro-5H-cyclopenta[d]pyrimidin-4-yl)oxy)benzonitrile (C4)

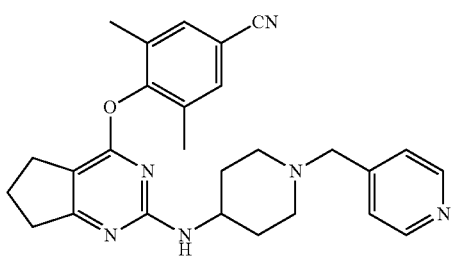 [SMILES: Cc1cc(C#N)cc(C)c1Oc1nc(NC2CCN(Cc3ccncc3)CC2)nc2c1CCC2]

Starting with 17 and 4-(chloromethyl)pyridine to afford C4 as a white solid. Yield: 72%, mp: 173-175° C.

白色固体, 收率, 72%, 熔点173-175° C. $^1$H NMR (400 MHz, DMSO-$d_6$) 8.57 (d, J=7.9 Hz, 2H, C$_3$,C$_5$-Ph'-H), 7.64 (s, 2H, C$_3$,C$_5$-Ph"-H), 7.28 (d, J=8.0 Hz, 2H, C$_2$,C$_6$-Ph'-H), 6.83 (s, 1H, NH), 3.60 (s, 1H), 3.48-3.42 (m, 2H), 2.76 (dt, J=21.6, 7.2 Hz, 4H), 2.70-2.62 (m, 2H), 2.07 (s, 6H), 2.02 (d, J=7.4 Hz, 2H), 1.85-1.21 (m, 6H). $^{13}$C NMR (100 MHz, DMSO-$d_6$) δ 168.2, 162.4, 142.9, 142.1, 133.7, 133.2, 129.5, 127.8, 1120.3, 108.7, 62.2, 52.6, 39.0, 31.6, 25.9, 22.0, 16.3. HRMS: m/z 455.2557 [M+1]$^+$. C$_{27}$H$_{30}$N$_6$O (454.2481).

3,5-dimethyl-4-((2-((1-(4-nitrobenzyl)piperidin-4-yl)amino)-6,7-dihydro-5H-cyclopenta[d]pyrimidin-4-yl)oxy)benzonitrile (C5)

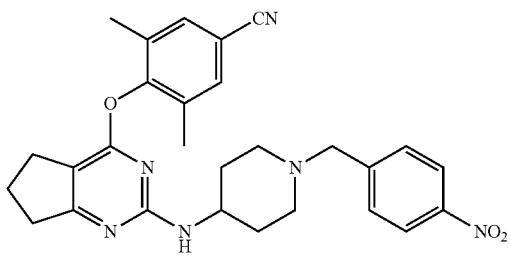

Starting with 17 and 1-(chloromethyl)-4-nitrobenzene to afford C5 as a white solid. Yield: 71%, mp: 200-212° C.

$^1$H NMR (400 MHz, DMSO-d$_6$) δ 8.17 (d, J=8.1 Hz, 2H, C$_3$,C$_5$-Ph'-H), 7.65 (s, 2H, C$_3$,C$_5$-Ph"-H), 7.54 (d, J=8.1 Hz, 2H), 6.80 (s, 1H, NH), 3.72 (s, 1H), 3.50 (s, 2H, N—CH$_2$), 2.78 (dd, J=14.4, 7.2 Hz, 4H), 2.71-2.64 (m, 2H), 2.07 (s, 6H), 2.03 (d, J=7.5 Hz, 2H), 1.81-1.23 (m, 6H). $^{13}$C NMR (100 MHz, DMSO-d$_6$) 159.7, 147.5, 146.9, 145.4, 139.8, 133.1, 132.6, 130.2, 127.4, 123.8, 108.3, 62.1, 61.7, 52.6, 44.1, 36.2, 31.6, 31.2, 25.9, 21.8, 16.2. HRMS: m/z 499.2456 [M+1]$^+$. C$_{28}$H$_{30}$N$_6$O$_3$ (498.2379).

3-((4-((4-(4-cyano-2,6-dimethylphenoxy)-6,7-dihydro-5H-cyclopenta[d]pyrimidin-2-yl)amino)piperidin-1-yl)methyl)benzamide (C6)

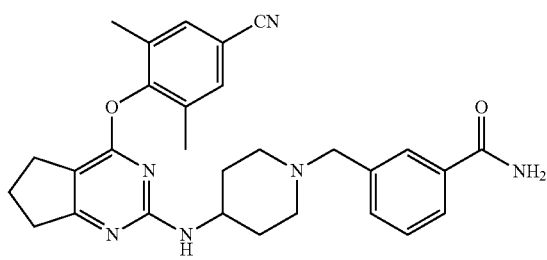

Starting with 17 and 3-(chloromethyl)benzamide to afford C6 as a white solid. Yield: 59%, mp: 234-236° C.

$^1$H NMR (400 MHz, DMSO-d$_6$) δ 7.96 (s, 2H, CONH$_2$), 7.79-7.75 (m, 1H), 7.65 (s, 2H, C$_3$,C$_5$-Ph"-H), 7.39-7.35 (m, 3H), 6.80 (s, 1H, NH), 3.72 (s, 1H), 3.50 (s, 2H, N—CH$_2$), 2.78 (dd, J=14.3, 7.2 Hz, 4H), 2.71-2.63 (m, 2H), 2.07 (s, 6H), 2.03 (d, J=7.5 Hz, 2H), 1.80-1.18 (m, 6H). $^{13}$C NMR (100 MHz, DMSO-d$_6$) 168.2, 162.3, 143.2, 142.5, 133.4, 133.1, 129.4, 128.8, 127.6, 119.5, 108.9, 62.2, 52.7, 39.0, 31.3, 25.9, 22.0, 16.3. ESI-MS: m/z 497.2657 [M+1]$^+$. C$_{29}$H$_{32}$N$_6$O$_2$ (496.2587).

Example 10: 4-((2-chloro-5,7-dihydrothieno[3,4-d]pyrimidin-4-yl)oxy)-3,5-dimethylbenzonitrile (19)

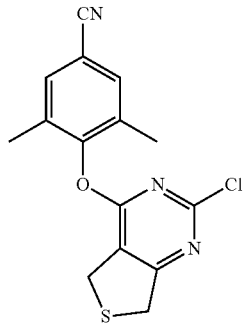

The synthetic method was similar to that described for 7, with the difference that the starting material was 2,4-dichloro-5,7-dihydrothieno[3,4-d]pyrimidine (18). White solid. Yield: 88%, mp: 268-270° C. $^1$H NMR (400 MHz, DMSO-d$_6$): δ 7.72 (s, 2H, C$_3$,C$_5$-Ph-H), 4.12 (s, 2H, S—CH$_2$), 4.07 (s, 2H, S—CH$_2$), 2.10 (s, 6H). ESI-MS: m/z 318.2 [M+1]$^+$. C$_{15}$H$_{12}$ClN$_3$OS (317.04).

Example 11: 3,5-dimethyl-4-((2-(piperidin-4-ylamino)-5,7-dihydrothieno[3,4-d]pyrimidin-4-yl)oxy)benzonitrile (21)

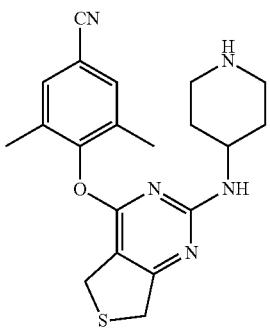

The synthetic method was similar to that described for 9, with the difference that the starting material was 19. White solid. Yield: 96%, mp: 268-270° C. H NMR (400 MHz, DMSO-d$_6$): δ 7.72 (s, 2H, C$_3$,C$_5$-Ph-H), 6.89 (s, 1H, NH), 4.12 (s, 2H, S—CH$_2$), 4.08 (s, 2H, S—CH$_2$), 3.72-3.70 (m, 1H), 2.74-2.72 (m, 2H), 2.10 (s, 6H), 1.97-1.75 (m, 4H), 1.47-1.42 (m, 2H). ESI-MS: m/z 382.2 [M+1]$^+$. C$_{20}$H$_{23}$N$_5$OS (381.16).

Example 12: Preparation of B1-B6

The synthetic method was similar to that described for A1-A6, with the difference that the starting material was compound 21.

4-((4-((4-(4-cyano-2,6-dimethylphenoxy)-5,7-dihydrothieno[3,4-d]pyrimidin-2-yl)amino)piperidin-1-yl)methyl)benzenesulfonamide (D1)

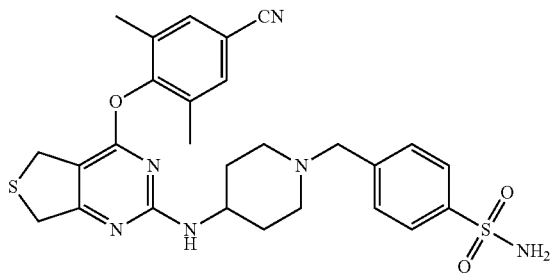 [SMILES: Cc1cc(C#N)cc(C)c1Oc1nc(NC2CCN(Cc3ccc(S(N)(=O)=O)cc3)CC2)nc2c1CSC2]

Starting with 21 and 4-(bromomethyl)benzenesulfonamide to afford D1 as a white solid. Yield: 79%, mp: 144-146° C.

$^1$H NMR (400 MHz, DMSO-$d_6$): δ 7.78 (d, J=8.2 Hz, 2H, $C_3$,C-Ph'-H), 7.72 (s, 2H, $C_3$,$C_5$-Ph"-H), 7.46 (d, J=8.1 Hz, 2H, $C_2$,$C_6$-Ph'-H), 7.30 (s, 2H, $SO_2NH_2$), 6.89 (s, 1H, NH), 4.12 (s, 2H, S—$CH_2$), 4.08 (s, 2H, S—$CH_2$), 3.72 (s, 1H), 3.42 (s, 2H, N—$CH_2$), 2.72-2.74 (m, 2H), 2.10 (s, 6H), 1.79-2.04 (m, 4H), 1.41-1.47 (m, 2H). $^{13}$C NMR (100 MHz, DMSO-$d_6$): δ 165.7, 161.7, 160.3, 153.7, 143.0, 135.3, 134.2, 126.0, 123.9, 123.7, 119.2, 109.7, 61.2, 52.8, 48.3, 31.7, 16.2. HRMS: m/z 551.1890 [M+1]*. $C_{27}H_{30}N_6O_3S_2$ (550.1821).

3,5-dimethyl-4-((2-((1-(4-(methylsulfonyl)benzyl)piperidin-4-yl)amino)-5,7-dihydrothieno[3,4-d]pyrimidin-4-yl)oxy)benzonitrile (D2)

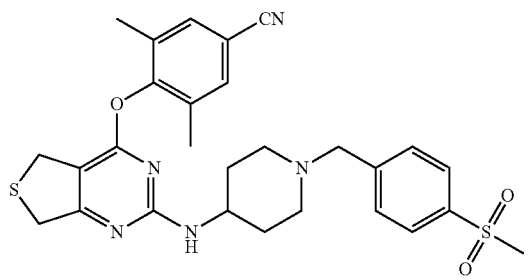 [SMILES: Cc1cc(C#N)cc(C)c1Oc1nc(NC2CCN(Cc3ccc(S(C)(=O)=O)cc3)CC2)nc2c1CSC2]

Starting with 21 and 4-(bromomethyl)benzenesulfonamide to afford D2 as a white solid. Yield: 71%, mp: 181-183° C.

$^1$H NMR (400 MHz, DMSO-$d_6$, ppm): δ 7.84 (d, 2H, J=8.2 Hz, $C_3$,$C_5$-Ph'-H), 7.71 (s, 2H, $C_3$,$C_5$-Ph"-H), 7.52 (d, 2H, J=8.2 Hz, $C_2$,$C_6$-Ph'-H), 6.88 (s, 1H, NH), 4.12 (s, 2H, S—$CH_2$), 4.08 (s, 2H, S—$CH_2$), 3.75-3.78 (m, 1H), 3.57 (s, 2H, N—$CH_2$), 3.06 (s, 3H, $SO_2CH_3$), 2.71-2.75 (m, 2H), 2.10 (s, 6H), 1.96-2.09 (m, 4H), 1.39-1.41 (m, 2H). $^{13}$C NMR (100 MHz, DMSO-d6): δ 165.1, 162.3, 159.4, 153.9, 145.2, 139.5, 134.3, 133.0, 126.8, 123.3, 118.9, 109.7, 62.3, 52.6, 48.5, 44.7, 32.0, 16.6. HRMS: m/z 550.1942 [M+1]$^+$. $C_{28}H_{31}N_5O_3S_2$ (549.1868).

Example 13. In Vitro Anti-HIV Activity of the Target Compounds

Selected compounds were screened for inhibitory activity against HIV-1 using MTT method as describe previously by Christophe. Pannecouque et al. *Nat. Protoc.* 3 (2008) 427-434, and Rudi Pauwels et al. *J. Virol. Methods* 20 (1988) 309-321. And in vitro anti-HIV activity of compounds were supported by Rega Institute for Medical Research. The MTT assay is based on the reduction of the yellow colored 3-(4,5-dimethylthiazol-2-yl)-2,5-diphenyltetrazolium bromide (MTT) by mitochondrial dehydrogenases of metabolically active cells to a blue formazan which can be measured spectrophotometrically. Tested optical density served as an indicator for live cells, and survival rate can be concluded by testing the optical density of 540 nm and 690 nm. MT-4 cells infected with HIV-1 can only survive for 5 to 7 days without any treatment, but when HIV-1 inhibitors were added, they can protect MT-4 cell from cytopathic. Serial solution of compounds was added to MT-4 cells after infected with HIV-1, MTT method was used to detect the survival rate after culture for 5 to 7 days. $EC_{50}$ value was defined as compound concentration required to achieve 50% protection of MT-4 cells against HIV-1-induced cytopathic effect.

Materials (1) MT-4 cells infected with HIV-1 viral strains (IIIB, Y181C/K103N) were provided by Rega Institute for Medical Research, Katholieke Universiteit Leuven, Belgium.

(2) MTT and formazan: sigma Chemical Co.

(3) Preparation of compounds: Stock solutions (10×final concentration) of test compounds is diluted with double distilled $H_2O$ for 5 folds and 5 concentrations of one compound are prepared.

(4) Reference drugs: Nevirapine (NVP) and Etravirine (ETR).

(5) Test method (MTT method): Serial five-fold dilutions of test compounds were added to cultured MT-4 cells infected with HIV-1, after 5 to 7 days, MTT was added and cultured for a few hours. Medium was removed and lysate was added followed by formazan, OD value was determined in 690 nm and 540 nm by microplate reader, and $EC_{50}$ value was calculated.

Methods

The MTT method was described briefly as follows: stock solutions (10×final concentration) of test compounds were added in 25 μL volumes to two series of triplicate wells in order to allow simultaneous evaluation of the effects on mock- and HIV-infected cells. Using a Biomek 3000 robot (Beckman Instruments, Fullerton, Calif.), serial five-fold dilutions of the test compounds (final 200 μL volume per well) were made directly in flat-bottomed 96-well microtiter trays, including untreated control HIV-1 and mock-infected cell samples for each sample. HIV-1 (IIIB) and mutant HIV-1 strains stock (50 μL at 100-300 $CCID_{50}$) or culture medium was added to either the infected or mock-infected wells of the microtiter tray. Mock-infected cells were used to evaluate the effect of test compounds on uninfected cells to assess cytotoxicity. Exponentially growing MT-4 cells were centrifuged for 5 min at 1000 rpm and the supernatant was discarded. The MT-4 cells were resuspended at 6×105 cells/mL, and 50 μL aliquots were transferred to the microtiter tray wells. At five days after infection, the viability of mock- and HIV-infected cells was determined spectrophotometrically by means of MTT assay.

The MTT assay is based on the reduction of yellow-colored MTT (Acros Organics, Geel, Belgium) by mitochondrial dehydrogenase of metabolically active cells to form a blue-purple formazan that can be measured spectrophotometrically. The absorbances were read in an eight-channel computer-controlled photometer, at the wavelengths of 540 and 690 nm. All data were calculated using the median optical density (OD) value of three wells. The $EC_{50}$ was defined as the concentration of the test compound affording 50% protection from viral cytopathogenicity. The $CC_{50}$ was defined as the compound concentration that reduced the absorbance ($OD_{540}$) of mock-infected cells by 50%. The results are shown in Table 1.

TABLE 1

The activity, cytotoxicity and SI values of the designed compounds

| 编号 | Ar | $EC_{50}$ (nM) IIIB | RES056 | $CC_{50}$ (μM) | SI IIIB | RES056 |
|---|---|---|---|---|---|---|
| A1 | 4-SO$_2$NH$_2$—Ph | 4.3 ± 0.7 | 28.8 ± 1.2 | 19.9 ± 10.1 | 4584 | 692 |
| A2 | 4-CONH$_2$—Ph | 4.8 | 43.6 ± 5.0 | 165 ± 36.9 | 34162 | 3804 |
| A3 | 4-SO$_2$CH$_3$—Ph | 5.9 ± 1.3 | 46.6 ± 7.8 | 11.9 ± 5.57 | 2025 | 257 |
| A4 | Pyridine-4-yl | 2.6 ± 1.0 | 46.0 ± 1.9 | ≥106 | ≥40104 | ≥2305 |
| A5 | 4-NO$_2$—Ph | 8.0 ± 1.7 | 495 ± 1.3 | 6.18 ± 1.74 | 770 | 12 |
| A6 | 3-CONH$_2$—Ph | 27.7 ± 21.5 | 629 ± 64.5 | ≥223 | ≥8048 | ≥355 |
| B1 | 4-SO$_2$NH$_2$—Ph | 2.0 ± 0.2 | 38.0 ± 7.5 | 22.9 ± 2.89 | 11167 | 604 |
| B2 | 4-CONH$_2$—Ph | 2.0 | 41.5 ± 9.9 | >250 | >125000 | >6039 |
| B3 | 4-SO$_2$CH$_3$—Ph | 1.8 | 41.6 ± 4.9 | 27.0 ± 3.03 | 14414 | 648 |
| B4 | Pyridine-4-yl | 2.8 | 43.1 ± 1.2 | 32.5 ± 10.0 | 11414 | 753 |
| B5 | 4-NO$_2$—Ph | 7.4 ± 0.9 | 511.1 ± 165.1 | ≥11.1 | ≥1497 | ≥22 |
| B6 | 3-CONH$_2$—Ph | 7.8 ± 3.4 | 1033 ± 51.1 | >250 | >31780 | >243 |
| C1 | 4-SO$_2$NH$_2$—Ph | 1.1 ± 0.5 | 25.8 ± 1.19 | >234 | >208333 | >9091 |
| C2 | 4-CONH$_2$—Ph | 6.1 ± 2.7 | 173 ± 110 | >251 | >40984 | >1448 |
| C3 | 4-SO$_2$CH$_3$—Ph | 1.8 ± 0.7 | 54.7 ± 6.22 | >274 | >147059 | >5020 |
| C4 | Pyridine-4-yl | 2.0 ± 0.5 | 26786 | 205 ± 1.13 | 124410 | 9 |
| C5 | 4-NO$_2$—Ph | 4.9 ± 0.8 | 187 ± 0.79 | 7.45 ± 0.930 | 1495 | 40 |
| C6 | 3-CONH$_2$—Ph | 14.5 ± 3.6 | 941 ± 368 | 8.73 ± 3.53 | 599 | 9 |
| D1 | 4-SO$_2$NH$_2$—Ph | 37.2 ± 26.6 | 734 ± 337.2 | 26.6 ± 1.96 | 715 | 36 |
| D2 | 4-SO$_2$Me—Ph | 3.8 ± 1.3 | 170 ± 32 | 45.3 ± 31.1 | 11690 | 266 |
| NVP | — | 163 ± 41.2 | >9513 | >9.51 | >58 | X1 |
| ETR | — | 5.1 ± 0.8 | 45.4 ± 15.5 | >4.59 | >889 | >101 |

$^a$$EC_{50}$: concentration of compound required to achieve 50% protection of MT-4 cell cultures against HIV-1-induced cytopathic, as determined by the MTT method.
$^b$$CC_{50}$: concentration required to reduce the viability of mock-infected cell cultures by 50%, as determined by the MTT method.
$^c$SI: selectivity index, the ratio of $CC_{50}/EC_{50}$.

What is claimed is:

1. A compound of five-membered non-aromatic pyrimidines derivative and its pharmaceutically acceptable, the compound having general formula I shown as following:

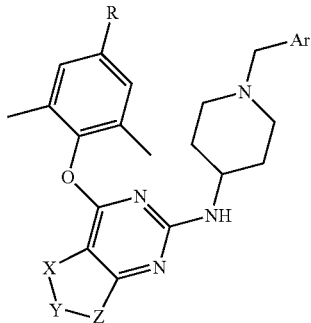

I wherein
R is CH$_3$, CN or CH=CHCN;
X is C, N, O, or S;
Y is C, N, O, or S;
Z is C, N, O, or S;
and at least two of X, Y and Z are C atoms at the same time;
Ar is one selected from the group consisting of phenyl, pyridyl, SO$_2$NH$_2$, SO$_2$NH$_2$CH$_3$, SO$_2$NH(CH$_2$)$_3$, SO$_2$NH(CH$_2$)$_2$O, SO$_2$CH$_3$, CONH$_2$, halogen, NO$_2$, CN, NH$_2$, CF$_3$, NHCH$_3$, OH, COOH, CH$_2$OH, CO$_2$Me, OCH$_3$, and NHCOCH$_3$ substituted phenyl; the NHCOCH$_3$ substituted phenyl is a single or multiple substitution(s) with orth-, meta- and para-.

2. The compound according to claim 1, wherein the compound is selected from the group consisting of:

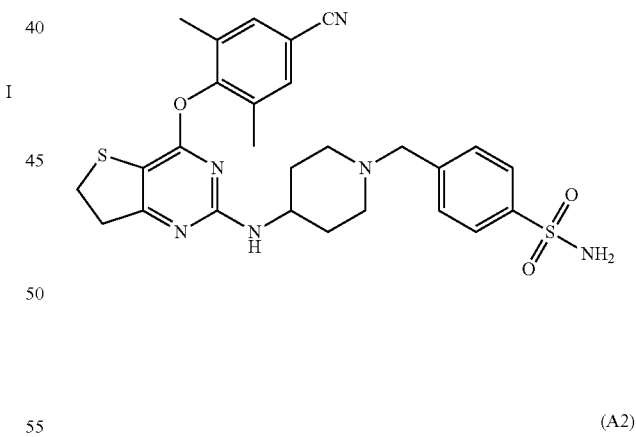

(A1)

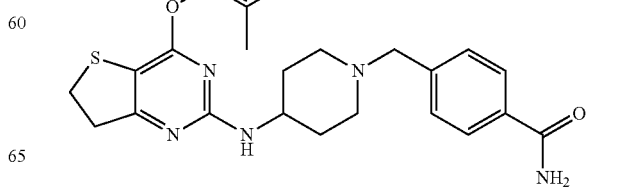

(A2)

(A3)
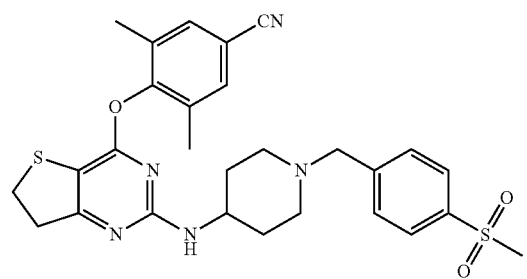
(A4)
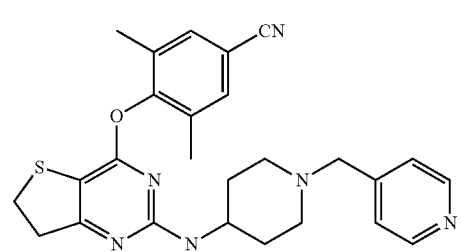
(A5)
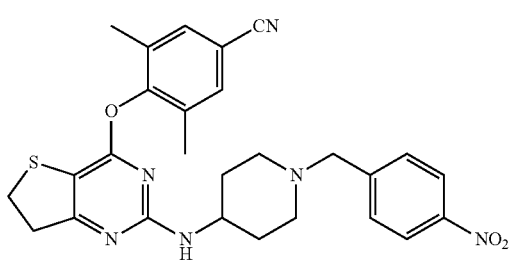
(A6)
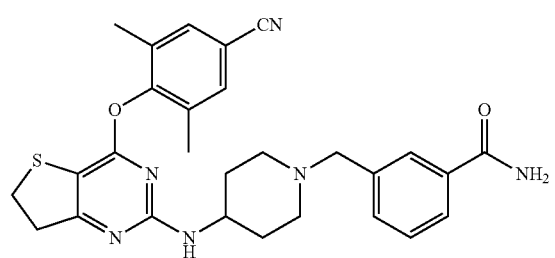
(B1)
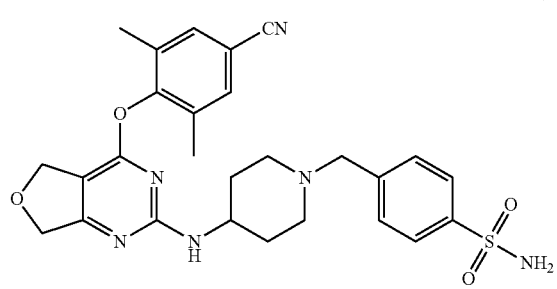
(B2)
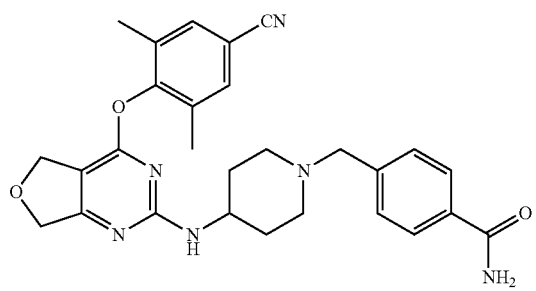
(B3)
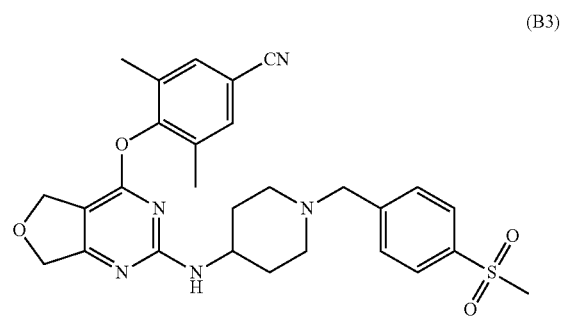
(B4)
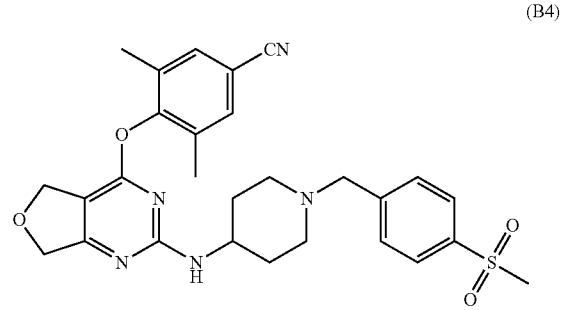
(B5)
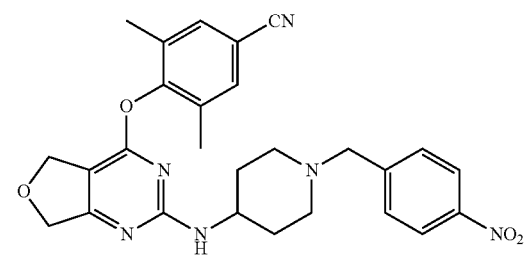
(B6)
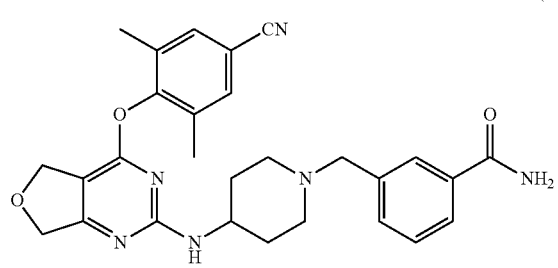

(C1) 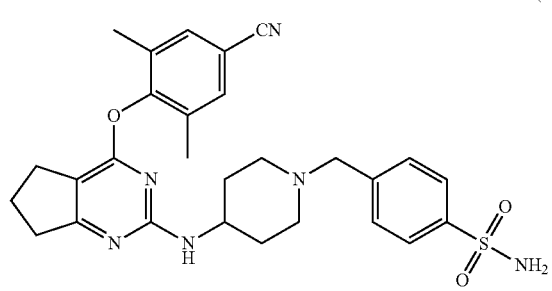

(C2) 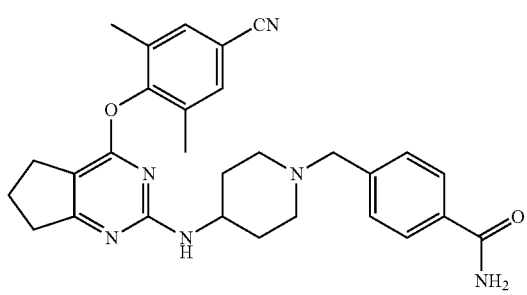

(C3) 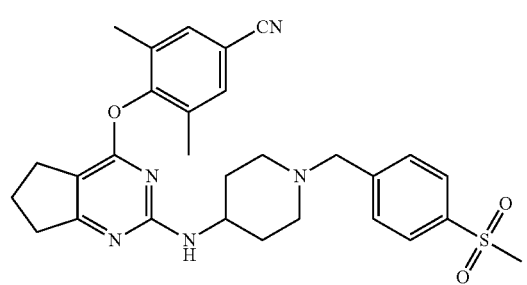

(C4) 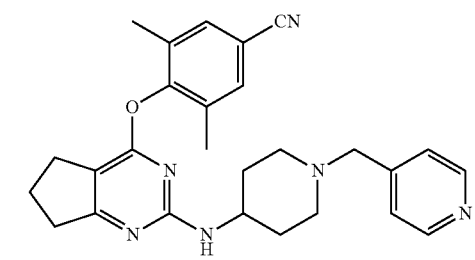

(C5) 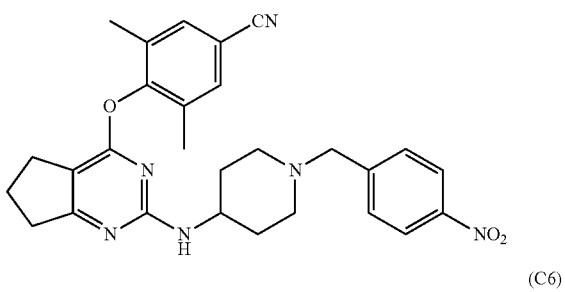

(C6) 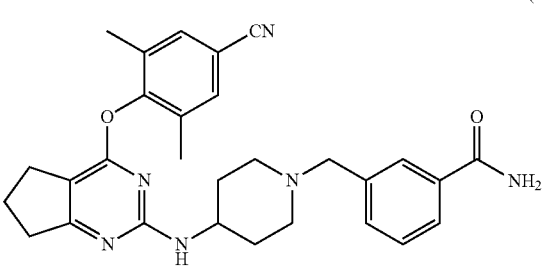

(D1) 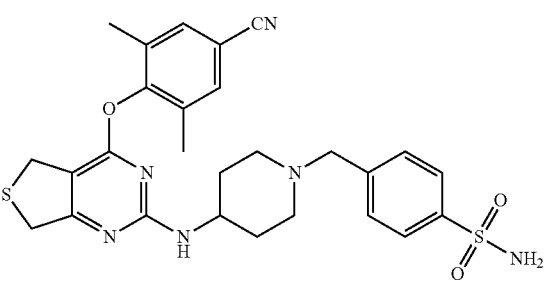

(D2) 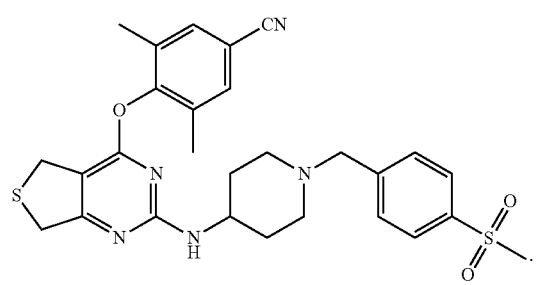

3. The compound according to claim 1, wherein the compound is prepared by the following steps: treating 2,4-dichloro-substituted five-membered non-aromatic pyrimidine 1 with substituted phenol or aniline, obtaining an intermediates 2 via nucleophilic substitution reaction; reacting the intermediates 2 with N-Boc-4-aminopiperidine, yielding an intermediate 3 which is deprotected with trifluoroacetic acid to yield an intermediate 4; then, converting the intermediate 4 into the compound by nucleophilic substitution with various substitutes of benzyl chloride or benzyl bromide;

wherein chemical reaction equations are as follows:

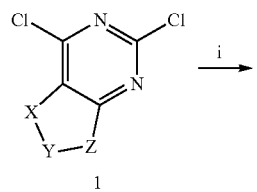

1

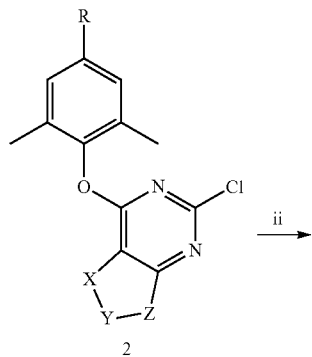

2

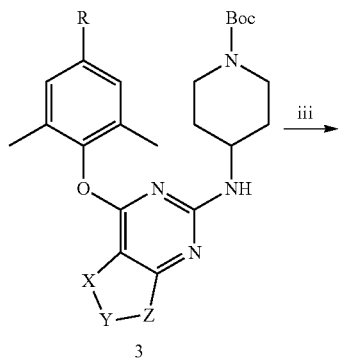

3

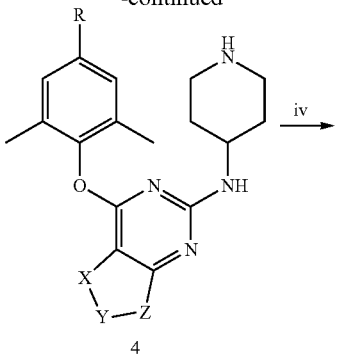

4

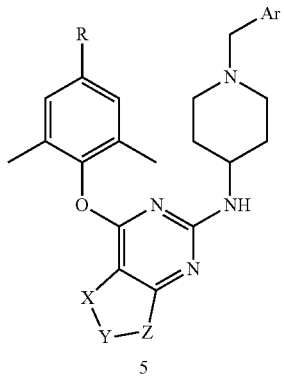

5 wherein (i) comprising substituted phenol or aniline, DMF and $K_2CO_3$; (ii) comprising N-Boc-4-aminopiperidine, DMF and $K_2CO$; (iii) comprising TFA and DCM; (iv) comprising substituted benzyl bromine, DMF and $K_2CO_3$.

4. A method for treating HIV-1 infection comprising a step of administering a subject infected with the HIV-1 with the compound of claim 1.

5. A pharmaceutical composition comprising the compound of claim 1, and one or more pharmaceutically acceptable carriers or excipients.

* * * * *